US010660856B2

(12) United States Patent
Monsuur

(10) Patent No.: US 10,660,856 B2
(45) Date of Patent: May 26, 2020

(54) POROUS SILICA GEL AS A CARRIER FOR LIQUID TECHNOLOGIES

(71) Applicant: W.R. Grace & Co.-Conn., Columbia, MD (US)

(72) Inventor: Frederik Hendrik Monsuur, Hasselt (BE)

(73) Assignee: W. R. Grace & Co.-Conn., Columbia, MD (US)

(*) Notice: Subject to any disclaimer, the term of this patent is extended or adjusted under 35 U.S.C. 154(b) by 0 days.

(21) Appl. No.: 14/764,363

(22) PCT Filed: Jan. 30, 2014

(86) PCT No.: PCT/US2014/013848
§ 371 (c)(1),
(2) Date: Jul. 29, 2015

(87) PCT Pub. No.: WO2014/120922
PCT Pub. Date: Aug. 7, 2014

(65) Prior Publication Data
US 2015/0366805 A1 Dec. 24, 2015

Related U.S. Application Data

(60) Provisional application No. 61/759,723, filed on Feb. 1, 2013.

(51) Int. Cl.
| | |
|---|---|
| *A61K 9/14* | (2006.01) |
| *A61K 9/20* | (2006.01) |
| *A61K 9/107* | (2006.01) |
| *B01J 20/10* | (2006.01) |
| *B01J 20/28* | (2006.01) |
| *C01B 33/193* | (2006.01) |

(52) U.S. Cl.
CPC ............... *A61K 9/143* (2013.01); *B01J 20/10* (2013.01); *B01J 20/103* (2013.01); *B01J 20/28004* (2013.01); *B01J 20/28059* (2013.01); *B01J 20/28073* (2013.01); *A61K 9/1075* (2013.01); *A61K 9/14* (2013.01); *A61K 9/2077* (2013.01); *C01B 33/193* (2013.01)

(58) Field of Classification Search
CPC .... B01J 2220/54; B01J 20/103; B01J 20/291; B01J 20/28078; B01J 20/3204; B01J 20/283; A61K 8/11; A61K 2800/56; A61K 8/0279; A61K 8/25; C01P 2006/12; C01P 2006/14; C01P 2006/16; C01B 33/12
See application file for complete search history.

(56) References Cited

U.S. PATENT DOCUMENTS

| | | | |
|---|---|---|---|
| 4,157,920 A | 6/1979 | Wason et al. ................. 106/292 |
| 4,226,743 A | 10/1980 | Seese et al. .................. 252/453 |
| 4,629,588 A * | 12/1986 | Welsh ....................... C11B 3/10 |
| | | | 423/339 |
| 5,256,386 A * | 10/1993 | Nystrom ............... B01J 20/103 |
| | | | 423/338 |
| 5,800,834 A | 9/1998 | Spireas et al. ................ 424/451 |
| 5,968,550 A | 10/1999 | Spireas et al. ................ 424/451 |
| 6,096,337 A | 8/2000 | Spireas et al. ................ 424/451 |
| 6,423,339 B1 | 7/2002 | Spireas ......................... 424/451 |
| 6,558,703 B1 | 5/2003 | Karlsson et al. ............. 424/489 |
| 6,596,314 B2 | 7/2003 | Wong et al. .................. 424/473 |
| 6,790,814 B1 | 9/2004 | Marin et al. .................. 510/101 |
| 7,488,533 B2 * | 2/2009 | Nishi ..................... A01N 25/08 |
| | | | 423/335 |
| 7,569,274 B2 | 8/2009 | Besse et al. |
| 7,674,764 B2 | 3/2010 | Leaym et al. ................ 510/466 |
| 7,691,400 B2 | 4/2010 | Francis ......................... 424/423 |
| 8,128,912 B2 | 3/2012 | Canham et al. ................ 424/59 |
| 2003/0152771 A1 | 8/2003 | Preston et al. |
| 2005/0112232 A1 | 5/2005 | Dollat et al. |
| 2006/0153912 A1 | 7/2006 | Habich et al. ................ 424/464 |
| 2006/0246151 A1 | 11/2006 | Anderson et al. ............ 424/617 |
| 2007/0003492 A1* | 1/2007 | Kitahata .................. A23G 4/06 |
| | | | 424/49 |
| 2007/0042046 A1 | 2/2007 | Saffie .......................... 424/482 |
| 2007/0125269 A1* | 6/2007 | Nishi ..................... A01N 25/08 |
| | | | 106/481 |
| 2007/0207942 A1 | 9/2007 | Creutz et al. ..................... 512/2 |
| 2008/0153694 A1* | 6/2008 | Nishi .................... C01B 33/128 |
| | | | 502/401 |
| 2009/0082447 A1 | 3/2009 | Berthoumieu et al. ....... 514/560 |

(Continued)

FOREIGN PATENT DOCUMENTS

| | | | |
|---|---|---|---|
| CN | 1682701 A | * 10/2005 | |
| EP | 0946154 | 11/2010 | ............... A61K 9/14 |

(Continued)

OTHER PUBLICATIONS

Chemical Book (Silica gel, https://www.chemicalbook.com/ProductCatalog_EN/1217.htm., copyright 2016).*
Kullenberg et al (Lipids in Health and Disease, Jan. 2012, vol. 11, pp. 1-16) (Year: 2012).*
Espinal (Characterization of Materials, Porosity and Its Measurement, 2012, pp. 1-9) (Year: 2012).*
CN 1682701 A, Espacenet English translation, downloaded in May 2019 (Year: 2019).*
Spomenka et al.; "An Oral Delivery System for Indomethicin Engineered from Cationic Lipid Emulsions and Silica Nanoparticles;" Journal of Controlled Release, 143 (2010), 367-373.
Wang et al.; "Calcium Phosphate/Block Copolymer Hybrid Porous Nanospheres: Preparation and Application in Drug Delivery;" Materials Letters, 64 (2010), 2299-2301.

(Continued)

*Primary Examiner* — Mark V Stevens

(57) ABSTRACT

Compositions containing a biologically active ingredient and an inorganic oxide material are disclosed. Methods of making and using compositions containing a biologically active ingredient and an inorganic oxide material are also disclosed. The present invention relates to compositions comprising inorganic oxide porous material containing a biologically active ingredient in liquid form, methods of making such compositions, and methods of using them.

24 Claims, 3 Drawing Sheets

(56) References Cited

U.S. PATENT DOCUMENTS

| | | | |
|---|---|---|---|
| 2009/0258812 A1 | 10/2009 | Sengupta et al. | 510/475 |
| 2009/0263486 A1 | 10/2009 | Prestidge et al. | 424/489 |
| 2009/0311159 A1* | 12/2009 | Gray | C01B 33/183 423/335 |
| 2010/0040565 A1 | 2/2010 | Homola et al. | 424/49 |
| 2010/0136105 A1* | 6/2010 | Chen | A61K 31/566 424/455 |
| 2010/0136124 A1 | 6/2010 | Prestidge et al. | 424/490 |
| 2010/0298447 A1 | 11/2010 | Fujii et al. | 514/783 |
| 2011/0020455 A1 | 1/2011 | Yoshida et al. | 424/489 |
| 2011/0037021 A1 | 2/2011 | Tschernjaew et al. | 252/182.13 |
| 2011/0229559 A1 | 9/2011 | Prestidge et al. | 427/2.14 |
| 2012/0269792 A1 | 10/2012 | Khan et al. | |
| 2015/0079182 A1 | 3/2015 | Shevachman et al. | 424/489 |
| 2015/0080217 A1 | 3/2015 | Knieriem et al. | 504/144 |

FOREIGN PATENT DOCUMENTS

| | | | |
|---|---|---|---|
| EP | 2251038 | 11/2010 | A61K 47/04 |
| JP | 2005307120 | 11/2005 | |
| WO | 2004069135 | 8/2004 | A61K 9/00 |
| WO | 2004073689 | 9/2004 | |
| WO | 2006119779 | 11/2006 | A61K 9/14 |
| WO | 2012032337 | 3/2010 | A61K 31/437 |
| WO | 2010063998 | 6/2010 | A61K 47/48 |
| WO | 2011144346 | 11/2011 | |

OTHER PUBLICATIONS

Milovic et al.; "Characterization and Evaluation of SOlid Self-Microemulsifying Drug Delivery Systems and Porous Carriers as Systems for Improved Carbamazepine Release;" International Journal of Pharmaceutics, 436 (2012), 58-65.

Kirstl et al, "Current View on Nanosized Solid Lipid Carriers for Drug Delivery to the Skin;" Journal of Biomedical Nanotechnology, vol. 6, No. 5 (2010).

Tang et al.; "Development of Solid Self-Emulsifying Drug Delivery Systems: Preparation Techniques and Dosage Forms;" Drug Discovery Today, vol. 13, No. 13/14 (2008).

Simovic, et al.; "Dry Hybrid Lipid-Silica Microcapsules Engineered from Submicron Lipid Droplets and Nanoparticles as a Novel Delivery System for Poorly Soluble Drugs;" Molecular Pharmaceuticals, vol. 6(3) (2009), 861-872.

Tiong, et al.; "Effects of Liquisolid Formulations on Dissolution of Naproxen;" European Journal of Pharmaceuticals and Biopharmaceutics, 73 (2009), 373-384.

Zhou et al.; "Encapsulation of Hydrophobic Anticancer Drug in Nano-Scale Porous Ceramic Materials for Photodynamic Therapy;" Journal of Porous Materials, vol. 18. No. 4 (2011).

Bin et al.; "Fabrication of Magnetite Hollow Porous Nanocryslal Shells as a Drug Carrier for Paclitaxel;" Journal of Materials Chemistry, vol. 20, No. 34 (2010).

Szepes, et al.; "Freeze-Casting Technique in the Development of Solid Drug Delivery Systems;" Chemical Engineering and Processing, 46 (2007), 230-238.

Simovic, et al; "Hybrid Lipid-Silica Microcapsules Engineered by Phase Coacervation of Pickering Emulsions to Enhance Lipid Hydrolysis;" Physical Chemistry Chemical Physics, vol. 12, No. 26 (2010), 7162-7170.

Satheeshbabu, N. et al.; "Liquisolid: A Novel Technique to Enhance Bioavailability;" Journal of Pharmacy Research, 4(1) (2011), 181-185.

Karmarkar, Amrit et al.; "Liquisolid Tablets: A Novel Approach for Drug Delivery;" International Journal of Health Research, 2(1) (2009), 45-50.

Seenivesan, A. et al.; "Lovastatin Nanoparticle Synthesis and Characterization for Better Drug Delivery;" The Open Biotechnology Journal, vol. 5 (2011), 28-32.

Hou et al.; "Luminescent Porous Silica Fibers as Drug Carriers;" Chemistry: A European Journal, vol. 16, No. 48 (2010).

Gu et al.; "Magnetic Luminescent Porous Silicon Microparticles for Localized Delivery of Molecular Drug Payloads;" Small, vol. 6, No. 22 (2010).

Prow, et al.; "Nanoparticles and Microparticles for Skin Drug Delivery," Advanced Drug Delivery Reviews, 63 (2011), 470-491.

Faraji et al.; "Nanoparticles in Cellular Drug Delivery;" Bioorganic & Medicinal Chemistry, 17 (2009), 2960-2962.

Mura et al.; "New Solid Self-Emulsifying Systems to Enhance Dissolulion Rate of Poorly Water Soluble Drugs;" Pharmaceutical Development and Technology, (2010), 1-8.

Horcajada et al; "Porous Metal-Organic-Framework Nanoscale Carriers as a Potential Platform for Drug Delivery and Imaging;" Nature Materials, vol. 9 (2010).

Vaccari et al.; "Porous Silicon as Drug Carrier for Controlled Delivery of Doxorubicin Anticancer Agent;" Microelectronic Engineering, 83 (2006), 1598-1601.

Patel et al.; "Preparation and in Vitro Characterization of Porous Carrier-Based Floating Microspheres of Modal Drug for Gastric Delivery," Journal of Young Pharmacists, vol. 3. No. 2 (2011) 97-104.

Gracia-Gonzalez et al.; "Production of Hybrid Lipid-Based Particles Loaded with Inorganic Nanoparticles and Active Compounds for Prolonged Topical Release;" International Journal of Parmaceutics, 382 (2009), 296-304.

Pelss et al.; "Release of Anticancer Drug Doxoruhicin from Biodegradable Polymer Coated Porous Hydroxyapatite Scaffolds;" Advanced Materials Research, vol. 284-286 (2011), 1770-1773.

Lim et al.; "Silica-Lipid Hybrid Microcapsules: Influence of Lipid and Emulsifier Type on In Vitro Performance;" International Journal of Pharmaceutics, 409 (2011), 297-306.

Wang et al. "Solid Self-Emulsifying Nitrendipine Pellets; Preparation and In Vitro / In Vivo Evaluation;" Internationai Journal of Pharmaceutics, 383 (2010), 1.6.

Takeuchi et al.; "Spherical Solid Dispersion Containing Amorphous Tolbutamide Embedded in Enteric Coating Polymers or Colloidal Silica Prepared by Spray-Drying Technique;" Chemical and Pharmaceutical Bulletin, 35(9) (1987), 3800-3806.

Munusamy et al.; "Targeted Drug Delivery Using Silica Xerogel Systems to Treat Diseases Due to Intracellular Pathogens;" Materials Science and Engineering C, 29 (2009), 2313-2318.

PCT Search Report and Written Opinion for PCT/US2014/013848; dated May 7, 2014.

"Aerosil Colloidal Silicon Dioxide for Pharmaceuticals—Technical Information"; p. 1-24 (2006).

Evonik Industries "Pharma Silica Insights: A Newsletter for Silica Excipients for Pharmaceutical Formulations"; No. 1 (2012).

Khetarpal et al. "Formulation Development of a Stable Solid Oral Dosage Form of Valproic Acid Using Colloidal Silica"; International Journal of Drug Delivery, 4 (2012), 266-274.

Shrivastava et al. "Design, Optimization, Preparation and Evaluation of Dispersion Granules of Valsartan and Formulation into Tablets"; Current Drug Delivery, vol. 6, No. 1, p. 28-37 (2009).

* cited by examiner

Acetaminophen

Ascorbic acid

POROUS SILICA GEL AS A CARRIER FOR LIQUID TECHNOLOGIES

TECHNICAL FIELD

The present invention relates to compositions comprising inorganic oxide porous material containing a biologically active ingredient in liquid form, methods of making such compositions, and methods of using them.

BACKGROUND

The oral route remains the preferred route of drug administration due to its convenience and good patient compliance. Major problems in oral drug formulations are the erratic and incomplete absorption throughout the gastrointestinal (GI) tract, resulting in low and variable bioavailability and lack of dose proportionality. These problems mainly result from poor aqueous solubility of the active ingredient. It has been reported that an estimated of existing pharmaceutical active ingredients and an even higher proportion of all newly developed drugs are poorly soluble or insoluble in water. This poses a major challenge to drug development, as there is a high need for producing suitable formulations to improve the solubility and bioavailability of such drugs.

Much research has been conducted into methods to cope with these problems. Methods that have been developed include the reduction of particle size of the drug by micronisation or nanonisation as to increase surface area, thereby increasing dissolution rate of the active ingredient. Further methods include solubilization in surfactant systems, water-soluble molecular complexes with cyclodextrins, converting the drug in amorphous form by lyophilization or formation of solid dispersions in hydrophilic carriers, microencapsulation, and the release from porous carrier materials.

One technique for promoting dissolution properties and oral bioavailability of poorly water-soluble drugs is by using them in liquid phase by dissolution or emulsion in non-volatile oils/lipids. Such systems have been referred to as lipid based drug delivery system (LBDDS). In these forms the active ingredient is already in solution so that the drug is present on molecular level, avoiding the dissolution step from the crystalline state. The drugs in liquid phase are typically filled into soft gelatin capsules. The latter give rise to drawbacks, such as complications in manufacturing, low manageability and portability, risks of leakage, limited shelf-life due to stability problems during storage caused by interactions between the components, oxidation of the lipid components, issues of compatibility of the liquid formulation with the capsule shell, criticality of storage temperature because of irreversible drugs/excipients precipitation at lower temperatures.

To overcome these problems, so-called liquisolid formulations have been developed, which are porous carrier materials wherein the drugs remain in liquid form. Liquisolid forms are obtained by conversion of drugs in liquid form into acceptably flowing non-adherent and compressible powder mixtures by blending with selected carriers and coating materials. These then are converted into solid dosage forms such as tablets, pellets, and capsules.

Due to increased wetting and surface area for dissolution, liquisolid dosage forms of water insoluble drugs show improved dissolution properties and bioavailability. This technique was successfully applied for low dose water-insoluble drugs. However, as loadability and release of the drugs from the carriers used is limited, formulation of insoluble drugs at higher doses is one of the limitations of the liquisolid technique. Another problem associated with liquisolid formulations is their decreased flowability when loaded with higher amounts of drugs in liquid form. This causes these materials difficult to process in pharmaceutical manufacturing. In order to have acceptable flowability and compactability, high levels of carrier and coating materials have to be added thereby increasing the weight and volume of the resulting dosage forms.

One type of lipid based drug delivery systems are the self-emulsifying drug delivery systems (SEDDS). This type of emulsion-based drug formulations can be used in soft gelatin capsules or as liquisolid formulations. SEDDS are isotropic and thermodynamically stable mixtures of drug, surfactant/cosurfactant, that, in contact with aqueous fluids, spontaneously form oil-in-water emulsions of droplets, ranging in droplet size approximately between 100-300 nm. Systems forming emulsions with droplets of less than 50 nm are referred to as self-micro-emulsifying drug delivery systems (SMEDDS), and even smaller droplet sizes as self-nanoemulsifying drug delivery system (SNEDDS). Self-emulsifying formulations spread readily in the gastrointestinal (GI) tract, where the digestive motility of the stomach and the intestine provide the agitation necessary for selfemulsification. These systems advantageously present the drug in dissolved form and the small droplet size provides a large interfacial area for the drug absorption. When compared with emulsions, which are sensitive and metastable dispersed forms, SEDDSs are physically stable formulations that are easy to manufacture. In particular for lipophilic drugs that exhibit limited and distorted absorption, these systems offer an improvement in the rate and extent of absorption resulting in more reproducible bioavailability.

Given the advantages of solid dosage forms, SEDDS, SNEDDS and SMEDDS have also been converted into solid-SEDDS, solid-SNEDDS or solid-SMEDDS (S-SEDDS, S-SNEDDS or S-SMEDDS) using liquisolid solidification procedures similar as described above. The resulting solid formulations in turn can be worked into various solid or semisolid dosage forms (tablets, pellets, capsules, creams, transdermal systems, etc.).

SUMMARY

It is an object of this invention to provide further carriers for use in the release of active ingredients of various nature. It is a further object of this invention to provide carriers that allow higher drug loading compared to known systems, showing desired dissolution release profiles and concomitant oral bioavailability characteristics. It is also an object of this invention to provide compact liquisolid dosage forms of high dose water-insoluble drugs, which are of acceptable size to patients. It is an object of this invention to provide liquisolid materials with optimum properties such as flow and bulk density. Still a further object concerns the provision of liquisolid formulations that have good flowability characteristics and can be easily processed in pharmaceutical manufacturing.

One or more of these objects and other advantages are attained by the various aspects and embodiments of the present invention.

In one embodiment, the present invention relates to a composition comprising porous inorganic oxide particles containing a biologically active ingredient in a liquid material, wherein the inorganic oxide particles possess (a) an oil adsorption of about 100 to about 500 ml/100 g; and (b) pores having a pore volume, as measured by nitrogen porosimetry, of about 0.5 cm$^3$/g greater; wherein the inorganic oxide particles remain free flowing at a weight ratio of liquid material to inorganic oxide particles of at least 1.5:1, or 1.6:1, or 1.7:1, or 1.8:1, or 1.9:1, up to 2:1.

In another embodiment, the present invention relates to a pharmaceutical composition comprising at least one pharmaceutical dosage formulating ingredient and a composition comprising porous inorganic oxide particles containing a biologically active ingredient in a liquid material, wherein the inorganic oxide particles possess (a) an oil adsorption of about 100 to about 500 ml/100 g; and (b) pores having a pore volume, as measured by nitrogen porosimetry, of about 0.5 cm$^3$ g or greater; wherein said inorganic oxide particles remain free flowing at a ratio of liquid material to inorganic oxide particles of at least 1.5:1, or 1.6:1, or 1.7:1, or 1.8:1, or 1.9:1, up to 2:1.

In an even further embodiment, the present invention relates to a method of making composition comprising porous inorganic oxide material containing a biologically active ingredient in a liquid material, wherein the inorganic oxide particles possess (a) an oil adsorption of about 100 to about 500 ml/100 g; and (b) pores having a pore volume, as measured by nitrogen porosimetry, of about 0.5 cm$^3$/g or greater; wherein said inorganic oxide particles remain free flowing at a weight ratio of liquid material to inorganic oxide particles of at least 1.5:1, or 1.6:1, or 1.7:1, or 1.8:1, or 1.9:1, up to 2:1.

In another embodiment, the present invention concerns a method of making a pharmaceutical and/or cosmetic composition comprising at least one pharmaceutical dosage formulating ingredient and a composition comprising porous inorganic oxide particles containing a biologically active ingredient in a liquid material, wherein the inorganic oxide particles possess (a) an oil adsorption of about 100 to about 500 ml/100 g; and (b) pores having a pore volume, as measured by nitrogen porosimetry, of about 0.5 cm$^3$/g or greater; wherein said inorganic oxide particles remain free flowing at a weight ratio of liquid material to inorganic oxide particles of at least 1.5:1, or 1.6:1, or 1.7:1, or 1.8:1, or 1.9:1, or at least 2:1.

In a further embodiment, the present invention relates to a composition comprising porous inorganic oxide particles containing a biologically active ingredient in a liquid material, wherein the inorganic oxide particles possess (a) an oil adsorption of about 100 to about 500 ml/100 g; (b) pores having a pore volume, as measured by nitrogen porosimetry, of about 0.5 cm$^3$/g or greater; and (c) a pore size distribution having a relative span of about 1.5 or less, or about 1.4 or less, or about 1.3 or less, or about 1.2 or less, or about 1.1 or less, or about 1.0 or less.

In another embodiment, the present invention concerns a composition comprising porous inorganic oxide particles containing a biologically active ingredient in a liquid material, wherein the inorganic oxide particles possess (a) an oil adsorption of about 100 to about 500 ml/100 (b) pores having a pore volume, as measured by nitrogen porosimetry, of about 0.5 cm$^3$/g or greater; and (c) a median pore size of 5 nm to 30 wherein said inorganic oxide particles remain free flowing at a ratio of liquid material to inorganic oxide particles of at least 1:1, or 1.3, or 1.5:1, or 1.6:1, or 1.7:1, or 1.8:1 or 1.9:1 at least 2:1.

In an even further embodiment, the present invention relates to a composition comprising porous inorganic oxide particles containing a biologically active ingredient in a liquid material, wherein the inorganic oxide particles possess (a) an oil adsorption of about 100 to about 500 ml/100 g; (b) pores having a pore volume, as measured by nitrogen porosimetry, of about 0.5 cm$^3$/g or greater; and (c) a median particle size of from 3 microns to 10 mm; wherein said inorganic oxide particles remain free flowing at a ratio of liquid material to inorganic oxide particles of at least 1:1, or 1.3, or 1.5:1, or 1.6:1, or 1.7:1, or 1.8:1, or 1.9:1, or at least 2:1.

In another embodiment, the present invention concerns a composition comprising porous inorganic oxide particles containing a biologically active ingredient in a liquid material, wherein the inorganic oxide particles possess (a) an oil adsorption of about 100 to about 500 ml/100 g; and (b) pores having a pore volume, as measured by nitrogen porosimetry of about 0.5 cm$^3$/g or greater; wherein said composition, after mixing the inorganic oxide particles and liquid material, decreases in volume of at least about 15% after resting, or at least about 20%, or at least about 25%, or at least about 30%, or at least about 35%, or at least about 40% after resting.

In a further embodiment, the present invention relates to a composition comprising porous inorganic oxide particles containing a biologically active ingredient in a liquid material, wherein the inorganic oxide particles possess (a) an oil adsorption of about 100 to about 500 ml/100 g; and (b) pores having an pore volume, as measured by nitrogen porosimetry, of about 0.5 cm$^3$/g or greater; wherein said composition, after mixing the inorganic oxide particles and liquid material, increases in bulk density by at least about 15% after resting, or at least about 20%, or at least about 25%, or at least about 30%, or at least about 35%, or at least about 40% after resting.

In another embodiment, the present invention concerns a composition comprising porous inorganic oxide particles containing a biologically active ingredient in a liquid material, wherein the inorganic oxide particles possess (a) an oil adsorption of about 100 to about 500 ml/100 g; and (b) pores having an pore volume, as measured by nitrogen porosimetry, of about 0.5 cm$^3$/g or greater; wherein, after mixing the inorganic oxide particles and liquid material and then resting for at least 2 hours, at least about 400 mg of said composition may be loaded into a zero size capsule. In another embodiment, at least about 410 ma, or at least about 420 mg, or at least about 430 mg of said composition may be loaded into a zero size capsule.

In an even further embodiment, the present invention relates to a composition comprising, porous inorganic oxide particles containing, a biologically active ingredient in a liquid material, wherein the inorganic oxide particles possess (a) an oil adsorption of about 100 to about 500 ml/100 g; (h) pores having an pore volume, as measured by nitrogen porosimetry, of about 0.5 cm$^3$/g or greater; and (c) a ratio of liquid material to inorganic oxide particles of at least 1:1; wherein at least 65% of the liquid material is desorbed from the particles upon desorption.

In one embodiment, the inorganic oxide material comprises porous particles comprising pores having a mean pore diameter in the range of about 5 nm to about 30 nm.

In another embodiment, the porous inorganic oxide material containing a biologically active ingredient in a liquid material is in the form of particles, i.e. particles of porous inorganic oxide material containing a biologically active ingredient in liquid form. The average diameter of the particles of porous inorganic oxide material of the invention may be in the range of from about 3 μm to about 5 mm.

The compositions of the invention may contain further liquid organic auxiliary materials such as oils, non-volatile solvents, and surfactants.

In one embodiment, the particles of porous inorganic oxide material containing a biologically active ingredient in a liquid material of the invention from a powder that is freeflowing. In a further embodiment, the powder has a Carr index of equal or lower than 25, or the powder has a Hausner index of about 1 to about 1.4. In one embodiment, the angle of repose of said powder is from about 30° to about 45°. These properties are measured before and after loading the biologically active ingredient on the porous inorganic oxide material.

In further embodiment, the composition comprising porous inorganic oxide material containing a biologically active ingredient in a liquid material has a bulk bulk density, after loading and resting during at least 2 hours, of at least 450 g/l.

Upon loading with a biologically active ingredient in a liquid material, the resulting loaded porous inorganic oxide material may show a limited (e.g. up to about 10%) or no increase, but in particular shows a decrease in volume when compared to the unloaded inorganic oxide porous material. In one embodiment, the decrease is up to about 30%, or up to about 20%, or up to about 10% (each % in this paragraph being volume/volume or v/v). Each of the changes in volume and/or density mentioned herein are after loading and resting up to 2 hours depending upon the liquid, and even up to 24 or 48 hours. In one embodiment, upon loading the inorganic oxide porous material with biologically active ingredient in a liquid material, a decrease of the volume or increase in density, in particular the particular decreases of volume or increases in density mentioned herein, during a time period of about 3 hrs, in particular of about 2 hrs is observed, after which time period no further decrease occurs and the volume stays substantially constant.

The compositions of the present invention advantageously do not show the substantial increase of volume that is typically observed when loading art-known silicas with a biologically active ingredient in a liquid material. This allows the manufacture of more compact dosage forms, which in turn contributes to better processability during pharmaceutical manufacturing and to better acceptability of the dosage forms by patients.

In a further aspect, the present invention concerns a pharmaceutical composition comprising at least one pharmaceutical dosage formulating ingredient and a composition comprising porous inorganic oxide material containing a biologically active ingredient in a liquid material, wherein the inorganic oxide material has the oil adsorption, the pore volume, and BET surface area, as specified herein. In one embodiment, the said composition comprising inorganic oxide porous material containing a biologically active ingredient is in the form of particles.

The present invention is further directed to methods of making the disclosed compositions. In one embodiment, the method of making a composition of the present invention comprises incorporating at least one biologically active ingredient in a liquid material into the porous inorganic oxide material having the oil adsorption, the pore volume, and BET surface area, as specified herein.

In a further aspect, the present invention concerns a method of making a pharmaceutical composition comprising at least one pharmaceutical dosage formulating ingredient and a composition comprising porous inorganic oxide material containing a biologically active ingredient in a liquid material, wherein the inorganic oxide material has the oil adsorption, the pore volume, and BET surface area, as specified herein, said method comprising combining said pharmaceutical dosage formulating ingredient with said composition.

The present invention is also directed to methods of using the disclosed compositions. In one embodiment, the method of using a composition of the present invention comprises administering a composition of the invention to a patient so as to deliver a biologically active material to the patient, wherein the composition comprises a porous inorganic oxide material containing a biologically active ingredient in a liquid material, wherein the inorganic oxide material has the oil adsorption, the pore volume, and BET surface area, as specified herein. The composition that is administered in particular is a pharmaceutical dosage form.

In one embodiment, the said inorganic oxide material is in the form of particles, in particular particles having an average diameter as further specified herein.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein.

DETAILED DESCRIPTION

Figure 1:
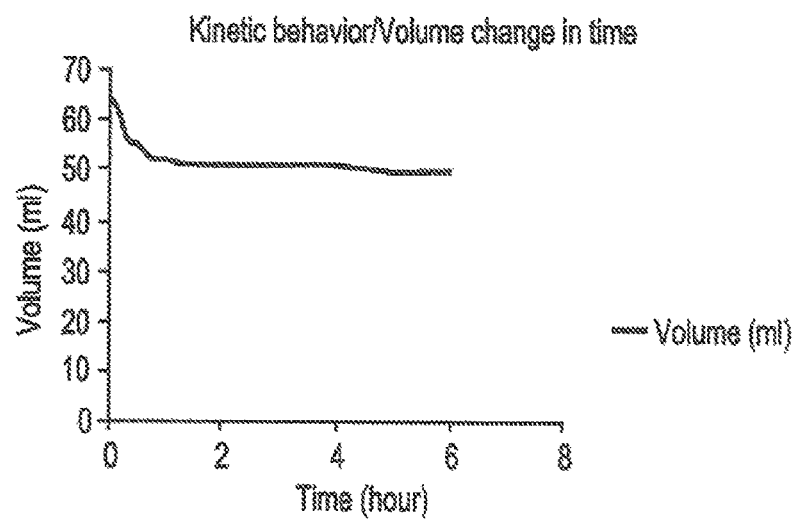
FIG. 1 graphically displays the kinetic behaviour or volume change over time of an exemplary composition of the present invention.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "an oxide" includes a plurality of such oxides and reference to "oxide" includes reference to one or more oxides and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the term "biologically active ingredient" means an active pharmaceutical ingredient (API), which provides a pharmacological activity or otherwise have direct effect in the diagnosis, cure, mitigation, treatment or prevention of disease, or to have direct effect in restoring, correcting or modifying physiological functions in humans. Even though this includes poorly soluble material, it may also include materials that range in solubility, including those listed in the BCS (Biopharmaceutic Classification System), which is a classification approach where drugs (APIs) are divided into four classes based on the extent (high or low) of their aqueous solubility and permeability through the GI tract wall, in particular intestinal. In this regard, these four classes are: (Group I) High Solubility and High Permeability drugs, (Group II) Low Solubility and High Permeability drugs, (Group III) High Solubility and Low Permeability drugs and, (Group IV) Low solubility and Low Permeability drugs.

As used herein, the term "bulk density" means the mass of particulate matter such as a powder, divided by the total volume occupied by the matter, and includes intraparticle pore volume and interparticle void volume.

As used herein, the terra "free flowing" means the ability of a group of particles or a powder to move when a force (e.g., gravity, or other external force) is applied to it. Commonly used tests for measuring powder flow include the Hausner compressibility index (Carr index) or angle of repose. The compressibility index (Carr index) and the Hausner ratio are determined by measuring both the bulk volume and the tapped volume of a powder.

As used herein, "inorganic oxides" is defined as binary oxygen compounds where the inorganic component is the cation and the oxide is the anion. The inorganic material includes metals may also include metalloids. Metals include those elements on the left of the diagonal line drawn from boron to polonium on the periodic table. Metalloids or semi-metals include those elements that are on the right of this line. Examples of inorganic oxides include silica, alumina, titanic, zirconia, etc., and mixtures thereof.

As used herein, the term "intraparticle pore volume" means pore volume attributable to the spaces in the pore of the particles, as compared to interparticle pore volume, which is the pore volume attributable to the spaces between the particles (i.e., the interstitial space).

As used herein, the term "lipid material" or "lipid component" means organic materials comprising fatty acids and their derivatives, and substances related biosynthetically or functionally to these compounds. They include, but are not limited to, molecules that originate entirely or in part by carbanion-based condensations of thioesters (fatty acids, polyketides, etc.) and/or by carocation-based condensations of isoprene units (prenols sterols, etc.).

As used herein, the term "ordered porous material" refers to porous particles that have an internal structural order such that they possess a low angle X-ray diffraction patterns according to Bragg's Law. Such materials include ordered mesoporous silica, for example, MCM-41, SBA-15, TUD-1, HMM-33 and FSM-16.

As used herein, the term "non-ordered porous material" refers to porous particles possessing an internal structure such that they do not have a low angle X-ray diffraction pattern according to Bragg's Law. Such materials may be formed via any known process including, but not limited to, a solution polymerization process such as for forming colloidal particles, a continuous flame hydrolysis technique such as for forming fused particles, a gel technique such as for forming gelled particles, and a precipitation technique such as for forming precipitated particles. The particles may be subsequently modified by autoclaving, flash drying, super critical fluid extracting, etching, or like processes. The particles may be composed of organic and/or inorganic materials and combinations thereof. In one exemplary embodiment the particles are composed of inorganic materials such as inorganic oxides, sulfides, hydroxides, carbonates, silicates, phosphates, etc, but are preferably inorganic oxides. The particles may be a variety of different symmetrical, asymmetrical or irregular shapes, including chain, rod or lath shape. The particles may have different structures including amorphous or crystalline, etc. The particles may include mixtures of particles comprising different compositions, sizes, shapes or physical structures, or that may be the same except for different surface treatments. Porosity of the particles may be intraparticle or interparticle in cases where smaller particles are agglomerated to form larger particles. In one exemplary embodiment the particles are composed of inorganic materials such as inorganic oxides, sulfides, hydroxides, carbonates, silicates, phosphates, etc, but are preferably inorganic oxides. Porous materials include organic and inorganic materials, or hybrids thereof, and may be in the form of particles, monoliths membranes, coatings, and the like.

As used herein, the term "pore size distribution" means the relative abundance of each pore size in a representative volume of porous inorganic particles. As used herein "median pore size" is the pore diameter below which 50% of the intraparticle pore volume resides.

As used herein, the term "relative span" is defined as meaning a measure of the breadth of pore size distribution. The "span" is measured by subtracting, the $d_{10}$ pore size (i.e., the pore size/diameter below which 10% of the pore volume resides) from the $d_{90}$, pore size (i.e., the pore size/diameter below which 90% by pore volume resides) as measured by mercury porosimetry. The term "relative span" is defined as the ratio of $(d_{90}-d_{10})/d_{50}$. The span and relative span are determined using nitrogen sorption (BJH method) of the cumulative pore volume.

As used herein the term "rested" or "after resting" is used to indicate a period of time wherein the porous inorganic oxide material is allowed to stand undisturbed after loading with a biologically active ingredient in a liquid material.

Whenever used herein in relation to a ratio or a percentage of components, w/w means weight/weight and w/v means weight/volume.

The present invention is directed to compositions comprising a biologically active material or ingredient and an inorganic oxide material, wherein the inorganic oxide material comprises porous particles. Efficient loading of biologically active materials in liquids or a liquid material onto vehicles for drug delivery is a concern for many biologically active materials and this invention relates to various embodiments that provide solutions to this problem. Applicants of the present invention have found that certain porous inorganic oxide materials having a specific sets of physical properties provide exceptional liquid loading and release of biologically active materials that are in various liquids or a liquid material.

In one embodiment, the present invention relates to a composition comprising porous inorganic oxide particles containing a biologically active ingredient in a liquid material, wherein the inorganic oxide particles possess (a) an oil adsorption of about 100 to about 500 ml/100 g; and (b) pores having a pore volume, as measured by nitrogen porosimetry, of about 0.5 $cm^3/g$ or greater; wherein the inorganic oxide particles remain free flowing at a weight ratio of liquid material to inorganic oxide particles of at least 1.5:1, or 1.6:1, or 1.7:1, or 1.8:1, or 1.9:1, up to 2:1.

In an even further embodiment, the present invention relates to a method of making composition comprising porous inorganic oxide material containing a biologically active ingredient in a liquid material, wherein the inorganic oxide particles possess (a) an oil adsorption of about 100 to about 500 ml/100 g; and (b) pores having a pore volume, as measured by nitrogen porosimetry, of about 0.5 $cm^3/g$ or greater; wherein said inorganic oxide particles remain free flowing at a weight ratio of liquid material to inorganic oxide particles of at least 1.5:1, or 1.6:1, or 1.7:1, or 1.8:1, or 1.9:1, up to 2:1.

In another embodiment, the present invention concerns a method of making a pharmaceutical composition comprising at least one pharmaceutical dosage formulating ingredient and a composition comprising porous inorganic oxide particles containing a biologically active ingredient in a liquid material, wherein the inorganic oxide particles possess (a) an oil adsorption of about 100 to about 500 ml/100 g; and (b) pores having a pore volume, as measured by nitrogen porosimetry, of about 0.5 $cm^3/g$ or greater; wherein said inorganic oxide particles remain free flowing at a weight ratio of liquid material to inorganic oxide particles of at least 1.5:1, or 1.6:1, or 1.7:1, or 1.8:1, or 1.9:1, or at least 2:1.

In another embodiment, the present invention concerns a composition comprising porous inorganic oxide particles containing a biologically active ingredient in a liquid material, wherein the inorganic oxide particles possess (a) an oil adsorption of about 100 to about 500 ml/100 g; (b) pores having a pore volume, as measured by nitrogen porosimetry, of about 0.5 $cm^3/g$ or greater; and (c) a median pore size of 5 nm to 30 am, wherein said inorganic oxide particles remain free flowing at a ratio of liquid material to inorganic oxide particles of at least 1:1, or 1.3, or 1.5:1, or 1.6:1, or 1.7:1, or 1.8:1, or 1.9:1, or at least 2:1.

In an even further embodiment, the present invention relates to a composition comprising porous inorganic oxide particles containing a biologically active ingredient in a liquid material, wherein the inorganic oxide particles possess (a) an oil adsorption of about 100 to about 500 ml/100 (b) pores having a pore volume, as measured by nitrogen porosimetry, of about 0.5 $cm^3/g$ or greater; and (c) a median particle size of from 3 microns to 10 mm; wherein said inorganic oxide particles remain free flowing at a ratio of liquid material to inorganic oxide particles of at least 1:1, or 1.3, or 1.5:1, or 1.6:1, or 1.7:1, or 1.8:1, or 1.9:1, or at least 2:1.

In a further embodiment, the present invention relates to a composition comprising porous inorganic oxide particles containing a biologically active ingredient in a liquid material, wherein the inorganic oxide particles possess (a) an oil adsorption of about 100 to about 500 ml/100 g; (b) pores having an pore volume, as measured by nitrogen porosimetry, of about 0.5 $cm^3/g$ or greater; and (c) a pore size distribution where at least 0.5 $cm^3/g$ of pore volume are from pores ranging from 10 nm to 30 nm, at least 0.5 $cm^3/g$, at least 0.6 $cm^3/g$ at least 0.8 $cm^3/g$, at least 1.0 $cm^3/g$, at least 1.2 $cm^3/g$, at least 1.4 $cm^3/g$, or at least 1.6 $cm^3/g$ of pore volume are from pores ranging from 10 nm to 30 nm.

In a further embodiment, the present invention relates to a composition comprising porous inorganic oxide particles containing a biologically active ingredient in a liquid material, wherein the inorganic oxide particles possess (a) an oil adsorption of about 100 to about 500 ml/100 g; (b) pores having a pore volume, as measured by nitrogen porosimetry, of about 0.5 $cm^3/g$ or greater; and (c) a pore size distribution having a relative span of about 1.5 or less, or about 1.4 or less, or about 1.3 or less, or about 1.2 or less, or about 1.1 or less, or about 1.0 or less.

The porous inorganic oxide material containing a biologically active ingredient in a liquid material may be in the form of particles, which may have a variety of different symmetrical, asymmetrical or irregular shapes, including chain, rod or lath shape. The particles may include mixtures of particles comprising different compositions, sizes, shapes or physical structures.

The average diameter of the particles of the porous inorganic oxide material of the invention may be in the range of from about 3 μm to about 5 mm, preferably from about 50 μm (or about 44 μm) to about 500 μm; or from about 70 μm (or about 74 μm) to about 200 μm; or from about 50 μm (or about 44 μm) to about 150 μm (or about 149 μm); or from about 50 μm (or about 44 μm) to about 150 μm (or about 149 μm); or from about 100 μm (or about 105 μm) to about 120 μm (or about 125 μm), or from about 48 μm (or about 44 μm) to about 65 μm (or about 63 μm), or from about 90 μm to about 130 μm. The average diameters disclosed herein preferably are determined by Malvern instrumentation. The desired particle sizes can be obtained by milling and subsequent mesh sieving.

The porous inorganic oxide materials may be formed via any known process including a solution polymerization process such as for forming colloidal particles, a continuous flame hydrolysis technique such as for forming fused particles, a gel technique such as for forming gelled particles, and a precipitation technique such as for forming precipitated particles. The particles may be subsequently modified by autoclaving, flash drying, super critical fluid extracting, etching, or like processes. In one embodiment the particles are composed of inorganic materials such as inorganic oxides, sulfides, hydroxides, carbonates, silicates, phosphates, etc, but are preferably inorganic oxides. The particles may include mixtures of particles comprising different compositions, sizes, shapes or physical structures, or that may be the same except for different surface treatments.

Porous materials include organic and inorganic materials, or hybrids thereof, and may be in the form of particles, monoliths, membranes, coatings, and the like.

The porous particles may be in various forms, such as precipitates, gels, fumed, colloidal, etc, and combinations thereof, unmodified or modified by subsequent processes, such as autoclaving, super critical fluid extraction, flash drying, and the like. In one embodiment, porous inorganic oxide material that is suitable for use in the present invention includes precipitated inorganic oxide particles and inorganic oxide gel particles. These inorganic oxides are referred to herein as “parent inorganic oxides”, “parent particles”, or “parent dispersions”.

In another embodiment, the porous inorganic oxide materials are non-ordered, and may further possess random intraparticle porosity. Such materials have been found, when combined with the biologically active ingredient and liquid material, to provide beneficial adsorption and desorption (and dissolution) characteristics. Even though any inorganic oxide composition may be suitable for use in this invention (e.g., $SiO_2$, $Al_2O_3$ $AlPO_4$, MgO, $TiO_2$, $ZrO_2$, etc.), one embodiment of the present invention includes amorphous precipitated silica and silica gel. The inorganic oxides may also include mixed inorganic oxides such as $SiO_2.Al_2O_3$, $MgO.SiO_2.Al_2O_3$ and the like. Mixed inorganic oxides are prepared by conventional blending or cogelling procedures. In embodiments comprising gels, the dispersions are derived from porous inorganic oxide gels such as gels comprising $SiO_2$, $Al_2O_3$, $AlPO_4$, MgO, $TiO_2$, and $ZrO_2$. The gels can be hydrogels, aerogels or xerogels.

In one embodiment, the inorganic oxide gels include a non-ordered porous silica gel that includes interparticle pore volume. Such a silica gel may be prepared by mixing an aqueous solution of an alkali metal silicate (e.g., sodium silicate) with a strong, acid such as nitric or sulfuric acid, the mixing being done under suitable condition's of agitation to form a clear silica sol which sets into a hydrogel, i.e., macrogel, in less than about one-half hour. The resulting gel is then washed. The concentration of inorganic oxide, i.e. $SiO_2$, formed in the hydrogel is usually in the range of about 10 and about 50, or between about 20 and about 35, or between about 30 and about 35 weight percent, with the pH of that gel being from about 1 to about 9, or 1 to about 4. A wide range of mixing temperatures can be employed, this range being typically from about 20 to about 50° C. The newly formed hydrogels are washed simply by immersion in a continuously moving stream of water, which leaches out the undesirable salts, leaving about 99.5 weight percent or more pure inorganic oxide behind. The pH, temperature, and duration of the washing will influence the physical properties of the silica, such as surface area (SA) and pore volume (PV). Silica gel washed at 65-90° C. at pH's of 8-9 for 15-36 hours will usually have SA's of 250-400 and form aerogels with PV's of 1.4 to 1.7 $cm^3/g$.

Methods for preparing inorganic oxide gels such as alumina and mixed inorganic oxide gels such as silica/alumina cogels are also well known in the art, such as by conventional blending, co-gelation, co-precipitation, and the like. Methods for preparing such gels have been described in U.S. Pat. No. 4,226,743. In general, alumina gels are prepared by mixing alkali metal aluminates and aluminum sulfate. Cogels are prepared by cogelling two or more metal oxides so that the gels are composited together. For example, silica alumina cogels can be prepared by gelling an alkali metal silicate with an acid or acid salt, and then adding alkali metal aluminate, aging the mixture and subsequently adding aluminum sulfate. The gel is then washed using conventional techniques. Another embodiment of this invention is derived from dispersions of certain precipitated inorganic oxides. Reinforced precipitated silica such as that described in U.S. Pat. No. 4,157,920 can also be used to prepare the dispersion of this invention. For example, reinforced precipitated silicas can be prepared by first acidulating an alkali inorganic silicate to create an initial precipitate. The resulting precipitate is then reinforced or "post conditioned" by additional silicate and acid. The precipitate resulting from the second addition of silicate and acid comprises 10 to 70% by weight of the precipitate initially prepared. It is believed that the reinforced structure of this precipitate is more rigid than conventional precipitates as a result of the second precipitation. Once an inorganic oxide is selected for the parent dispersion, a liquid phase of the selected inorganic oxide is prepared. In general, the parent dispersion should be in a state that can be wet milled. The medium for the liquid phase can be aqueous or non-aqueous, e.g., organic. The liquid phase can be residual water in inorganic oxide gels which have been drained, but not yet dried, and to which additional water is added to reslurry the gel.

In another embodiment, dried inorganic oxides, e.g., xerogels, are dispersed in liquid medium. In some embodiments, the parent dispersion is then milled. The milling is conducted "wet", i.e., in liquid media. The general milling conditions can vary depending on the feed material, residence time, impeller speeds, and milling media particle size. The techniques for selecting and modifying these conditions to obtain the desired dispersions are known to those skilled in the art. The milling equipment used to mill the parent inorganic oxide particles should be of the type capable of severely milling and reducing materials to particles having the desired size, e.g., through mechanical action. Such mills are commercially available, with fluid energy mills, hammer mills, and sand mills being particularly suitable for this purpose. Hammer mills impart the necessary mechanical action through high speed metal blades, and sand mills impart the action through rapidly churning media such as zirconia or sand beads. Impact mills can also be used. In other embodiments, milling is not needed, such as for air-set inorganic oxide gels. Such gels are formed by air-spraying an intimate mixture of an alkali metal solution (e.g., sodium silicate) with a suitable acid (e.g., sulfuric acid) at such a concentration so that mixture gels during flight, before being collected in a suitable medium, generally water. Any resulting dispersion or powder may also be further processed. For example, further processing is desirable if there is a need to prepare a relatively stable dispersion without the aid of dispersing agents, or if there is a significant population of particles that are larger than desired. Further processing may also be needed to insure that essentially all of the distribution of particles is below a certain size. In such a case, the dispersion or powder is processed to separate the smaller particles from the larger particles. This separation can be created by centrifuging the inorganic oxide particles into a supernatant phase, which comprises the smaller particles of the final product, and a settled phase which comprises the larger particles. The supernatant phase is then removed from the settled phase, e.g., by decanting. In some instances, it may be preferable to centrifuge the supernatant two, three or more times to further remove large particles remaining after the initial centrifuge. It is also contemplated that the larger particles of a milled dispersion can separate over time under normal gravity conditions, and the supernatant can be removed by decanting. Depending on the product particle size targets, the settled phase also can be regarded as particles of this invention. The dispersion of particles or powder also can be modified after milling to insure a stable dispersion. This can be accomplished through pH adjustment, e.g., adding alkaline material, or by the addition of conventional dispersants.

The inorganic oxide material in the compositions of the present invention may comprise two or more different and distinct types of porous particles. In one embodiment each type of porous particles provides a specific desorption and/or dissolution rate profile for the biologically active material in a liquid material so as to form a composite desorption and/or dissolution rate profile for the biologically active material.

In one embodiment, the surface of the inorganic oxide material, in particular the surface in the pores, has not been chemically modified. The pores in the inorganic oxide material are open so that the active ingredient in a liquid material can enter the pores and become adsorbed at the surface of the pores, or can leave the pores as to release the active ingredient.

The porous inorganic oxide material of the present invention has an oil adsorption of about 100 to about 600 ml/100 g, or of about 100 to about 500 ml/100 g, or of about 100 to about 450 ml/100 g, or of about 100 to about 400 ml/100 g, or of about 150 to about 400 ml/100 g, or of about 200 to about 400 ml/100 g. The oil adsorption values can be measured with standard methodology, in particular by titrating a predetermined quantity of the inorganic oxide material with an oil under constant mixing of the oil/inorganic oxide material, until the mass shows excess of oil, such as done in ASTM D281.

The inorganic oxide material in the compositions of the present invention is porous. In one embodiment the pores have a mean pore diameter of greater than 5 nm, or from about 5 nm to about 30 nm; or from about 10 nm to about 30 nm. In a further embodiment, the mean pore diameter is about 20 to about 25 urn.

Desirably, the porous inorganic oxide material has a pore volume of about 0.5 cm$^3$/g or greater, or about 0.6 or greater, or about 0.7 cm$^3$/g or greater. In some embodiments, the upper limit of the pore volume is about 3.0 cm$^3$/g, or about 2.3 cm$^3$/g.

Desirably, the porous inorganic oxide material has a BET surface area, as measured by nitrogen adsorption, of about 10 m$^2$/g or greater, or about 100 m$^2$/g or greater, or of about 200 m$^2$/g or greater, or of about 300 m$^2$/g or greater. In some embodiments, the upper limit of the BET surface area is about 1000 m$^2$/g, or about 800 or of about 600 m$^2$/g. In other embodiments, the BET surface area may range from about 10 to about 1000 or about 100 to about 800 m$^2$/g, or about 150 to about 600 m$^2$/g, or about 200 to about 500 m$^2$/g, or about 250 to about 400 m$^2$/g.

In one embodiment, the porous inorganic oxide material has (i) a mean pore diameter of from about 5 nm to about 30 nm, (ii) a pore volume of about 03 cm$^3$/g or greater, and (iii) a surface area of about 20 to about 500 m$^2$/g, or greater. In another embodiment, this porous inorganic oxide material is in the form of particles, which may have a diameter from about 50 μm (or about 44 μm) to about 150 μm (or about 149 μm). In a further embodiment, this inorganic oxide porous material has an oil adsorption of about 100 to about 500 ml/100 g. Such materials are attractive due to their superior properties in terms of high loading, bulk density, flowability, desorption and dissolution characteristics.

In the present invention, the measurements of pore volume are generated by N$_2$ porosity analysis and surface area are generated by the BET technique, which are art-known techniques.

The porous inorganic oxide material containing a biologically active ingredient in a liquid material may be obtained from porous inorganic oxide material that do not contain a biologically active ingredient in a liquid material, which biologically active ingredient in a liquid material subsequently is added so that it is adsorped by the porous inorganic oxide material. Or, alternatively, the biologically active ingredient in a liquid material may be added during one or more of the steps of the preparation of the porous inorganic oxide material.

In yet another embodiment, the inorganic oxide can be dispersed in a liquid compound, which is subsequently used as a reactant or solvent or medium, which forms the biologically active composition of the present invention.

The particles of porous inorganic oxide material of the invention may be free-flowing. In one embodiment said particles may have a Carr index of equal or lower than about 25, e.g. a Carr index of about 10 to about 25. In some embodiments the Carr index may be equal or lower than about 15, e.g. a Carr index of about 10 to about 15. The particles of porous inorganic oxide material of the invention may have a Hausner index of about 1 to about 1.4, in particular of about 1.2 to about 1.4. The particles of porous inorganic oxide material of the invention may have an angle of repose of about 30° to about 45°. In some embodiments, the Carr and Hausner index values and angles of repose mentioned herein apply to any of the particles of the invention having a w/w ratio of the biologically active ingredient in a liquid material to inorganic oxide inorganic oxide, as specified herein, and in particular where said w/w ratio is between about 0.5:1 to about 2:1. In some embodiments, the Can and Hausner index values and angles of repose mentioned herein apply to any of the particles of the invention that are unloaded with biologically active ingredient in a liquid material.

The Carr index (C.I.) is an indication of the flowability and compressibility of a powdery material and is calculated by the formula $C=100 \times (1-\rho_b/\rho_t)$, where $\rho_b$ is the freely settled bulk bulk density of a powder, and $\rho_t$ is the tapped bulk density of the powder. A Carr index greater than 25 is considered to be an indication of poor flowability. Materials having a Carr index equal to or lower than 25 show good flowability and can also be referred to as "free-flowing" materials. The Hausner index (H.I.) is calculated by the formula $H=\rho_t/\rho_b$.

In another embodiment, the present invention concerns a composition comprising porous inorganic oxide particles containing a biologically active ingredient in a liquid material, wherein the inorganic oxide particles possess (a) an oil adsorption of about 100 to about 500 ml/100 g; and (b) pores having a pore volume, as measured by nitrogen porosimetry, of about 0.5 cm$^3$/g or greater; wherein said composition, after mixing the inorganic oxide particles and liquid material, decreases in volume of at least about 15% after resting, or at least about 20%, or at least about 25%, or at least about 30%, or at least about 35%, or at least about 40% after resting. Each of the changes in volume and/or density mentioned herein are after loading and resting up to 2 hours depending upon the liquid, and even up to 24 or 48 hours. In one embodiment, upon loading the inorganic oxide porous material with biologically active ingredient in a liquid material, a decrease of the volume or increase in density, in particular the particular decreases of volume or increases in density mentioned herein, during a time period of about 3 hrs, in particular of about 2 hrs is observed, after which time period no further decrease occurs and the volume stays substantially constant.

In a further embodiment, the present invention relates to a composition comprising porous inorganic oxide particles containing a biologically active ingredient in a liquid material, wherein the inorganic oxide particles possess (a) an oil adsorption of about 100 to about 500 ml/100 g; and (b) pores having an pore volume, as measured by nitrogen porosimetry, of about 0.5 cm$^3$/g or greater; wherein said composition, after mixing the inorganic oxide particles and liquid material, increases in bulk bulk density by at least about 15% after resting, or at least about 20%, or at least about 25%, or at least about 30%, or at least about 35%, or at least about 40% after resting. Each of the changes in volume and/or density mentioned herein are after loading and resting up to 2 hours depending upon the liquid, and even up to 24 or 48 hours. In one embodiment, upon loading the inorganic oxide porous material with biologically active ingredient in a liquid material, a decrease of the volume or increase in density, in particular the particular decreases of volume or increases in density mentioned herein, during a time period of about 3 hrs, in particular of about 2 hrs is observed, after which time period no further decrease occurs and the volume stays substantially constant.

In another embodiment, the present invention concerns a composition comprising porous inorganic oxide particles containing a biologically active ingredient in a liquid material, wherein the inorganic oxide particles possess (a) an oil adsorption of about 100 to about 500 ml/100 g; and (b) pores having an pore volume, as measured by nitrogen porosimetry, of about 0.5 cm$^3$/g or greater, wherein, after mixing the inorganic oxide particles and liquid material and then resting for at least 2 hours, at least about 400 mg of the composition may be loaded into a zero size capsule. In another embodiment, at least about 410 mg, or at least about 420 mg, or at least about 430 mg of said composition may be loaded into a zero size capsule.

In an even further embodiment, the present invention relates to a composition comprising porous inorganic oxide particles containing a biologically active ingredient in a liquid material, wherein the inorganic oxide particles possess (a) an oil adsorption of about 100 to about 500 ml/100 g; (b) pores having an pore volume, as measured by nitrogen porosimetry, of about 0.5 cm$^3$/g or greater; and (c) a ratio of liquid material to inorganic oxide particles of at least 1:1; wherein at least 65% of the liquid material is desorbed from the particles upon desorption. In another embodiment, at least 70%, or at least 75%, or at least 80%, or at least 85% of the liquid material is desorbed from the particles upon desorption. The liquid material is desorbed under conditions that simulate desorption of liquid material in biological fluids. Such tests are performed by intense mixing in aqueous medium, as set forth in Example 7.

As used herein, the term "in liquid form" or "liquid material" in relation to biologically active ingredients refers to such ingredients that in themselves are liquids or to biologically active ingredients brought into liquid form by various techniques including, for example, desorption and/ or dissolution or conversion into a self-emulsifying drug delivery system. Such materials may also include solid biologically active ingredients that are suspended, dispersed or incorporated with liquids.

The term "in liquid form" or "liquid material" refers to biologically active ingredients as such or brought into liquid form that are liquid at room temperature or at physiological temperature, or are liquid at temperatures ranging from about 0° C. to about 60° C., in particular about 10° C. to about 50° C., or about 20° C. to about 45° C. Such materials may be solid at certain conditions (e.g., temperature, concentration, etc.) and liquid under other conditions.

The porous inorganic oxide material in accordance with this invention contains a biologically active ingredient in liquid form. The term "contain" means that the porous inorganic oxide material is loaded with a biologically active ingredient, the term "loaded" meaning that the active ingredient is adsorbed at the surface of the inorganic oxide material, including the surface within the pores of the inorganic oxide material. A major part of the active ingredient may be incorporated in the pores of the inorganic oxide material. Such inorganic oxide materials with adsorbed biologically active ingredient are referred as "loaded inorganic oxide materials". The terms "loaded" and "incorporated" in this context are meant to be equivalent.

In one embodiment, the w/w ratio of the biologically active ingredient in a liquid material (which comprises the biologically active ingredient itself as well as any added materials in the liquid) to inorganic oxide is in the range of about 0.5:1 to about 5:1, or of about 0.5:1 to about 3:1, or of about 0.5:1 to about 2:1, or of about 1:1 to about 2:1.

The composition comprising porous inorganic oxide material containing a biologically active ingredient in a liquid material may have a bulk density of at least 450 g/l. In some embodiments said bulk density is in the range of from 450 g/l to 750 g/l, in particular in the range of from 500 g/l to 700 g/l, or in the range of from 550 g/l to 650 g/l.

In one embodiment, the biologically active ingredient in a liquid material is a liquid lipid drug. Examples include vitamin A, vitamin E (dl-α-Tocopherol), paracetamol, ascorbic acid, sesame oil, miglyol, or combinations thereof.

In another embodiment the biologically active ingredient in a liquid material takes the form of a solution or dispersion of the biologically active ingredient in a non-volatile solvent, e.g. having a boiling point of above about 150° C. Examples include glycerin, propylene glycol, liquid polyethylene glycols such as polyethylene glycol 200 and 400, polysorbates such as polysorbate 80, or an oil. Oils that can be used include long-chain triglyceride and medium-chain triglyceride oils with different degrees of saturation; vegetable oils such as olive oil, sunflower oil, castor oil, linseed oil and the like; modified or hydrolyzed vegetable oils; semisynthetic medium-chain triglyceride oils having surfactant properties, for example Cremophor. In case of dispersions, the active ingredient is preferably in the form of micro- or of nanoparticles. In one embodiment, the concentration of the biologically active ingredient in the solution or dispersion is in the range of from 1% to 90%, or from . . . (w/w).

In one embodiment the biologically active ingredient in a liquid material is a self-emulsifying drug delivery system (SEDDS) comprising an oily/lipid component, a surfactant, cosolvent, and a biologically active ingredient.

The oily/lipid component is generally a fatty acid ester or a medium/long chain saturated, partially unsaturated or unsaturated hydrocarbon, in liquid, semisolid or solid form at room temperature (e.g., solid lipid nanoparticles, oily suspensions, submicron lipid emulsions, lipid implants, lipid microtubules, lipid microbubbles, or lipid microspheres, etc.). Examples include mineral oil, vegetable oil, modified or hydrolyzed vegetable oils, silicone oil, lanolin, liposomes, refined animal oil, fatty acids, fatty alcohols, and mono-/ di-/tri-glycerides, including long-chain triglyceride and medium-chain triglyceride oils with different degrees of saturation and semisynthetic medium-chain triglyceride oils having surfactant properties. Further oily/lipid components include oils comprised of one or more medium chain fatty acids esters of propylene glycol such as propylene glycol monocaprate, propylene glycol dicaprate, propylene glycol dicaprylate/dicaprate, propylene glycol dipelargonate, and propylene glycol dilaurate, triacetin, fats and oils such as olive oil, sesame oil, soybean oil, corn oil, rape oil, castor oil, coconut oil, and eucalyptus oil; caprylic/capric acid triglyceride (Miglyol™ 812); a triglyceride such as tricaprylin and trilaurin; and polyglycerin fatty acid esters such as tetraglycerin polyricinoleate, hexaglycerin polyricinoleate, condensed polyricinoleate, and tetraglycerin mixed fatty acid esters. The term "medium chain fatty acid" is meant to refer to fatty acyl chains of between 6 and 14 carbons in length, more preferably between 8 and 12 carbons in length; "long chain fatty acid" is meant to refer to fatty acyl chains greater than 14 carbons in length; "short chain fatty acid" is meant to refer to fatty acyl chains less than 6 carbons in length.

The oil components may be used in the SEDDS formulations of the present invention in any effective concentration, including, for example, in a concentration range of 5% to 80% (w/v).

Preferred surfactants comprise non-ionic surfactants with a relatively high hydrophilic-lipophilic balance (HLB) value usually in concentration ranges between 30% and 60% (w/w).

The hydrophilic surfactant (HLB (hydrophile-lipophile balance) of 9.0 or higher that can be used include polyoxyethylene lauryl ethers (Laureth 2 (BL-2), Laureth 4.2 (BL-4.2), and Laureth 9 (BL-9), polyoxyethylene (20) sorbitan monococonut oil fatty acid ester ("Polysorbate 20"), Polysorbate 40, Polysorbate 80, Labrasol, D-α-tocopheryl polyethylene glycol 1000 succinate (Vitamin E TPGS NF), lauroyl polyoxyethylene glycerin (Gelucire 44/14), polyoxyethylene hydrogenated castor oil 40, polyoxyethylene hydrogenated castor oil 60 (HCO-60), polyoxyethylene sorbitan monolaurate, polyoxyethylene sorbitan monopalmitate, and polyoxyethylene sorbitan monooleate.

Any effective non-aqueous protic cosolvent, or combinations thereof, may be used in the SEDDS for use in the invention. Acceptable non-aqueous protic solvents include any pharmaceutically acceptable mono-, di-, tri-, or polyhydroxy linear aliphatic and aromatic solvent, or combinations thereof. Examples of non-aqueous protic solvents include ethanol, propanol, benzyl alcohol, propylene glycol, liquid polyethylene glycols such as polyethylene glycol 200 and 400, and glycerol. The protic solvents may be used in the formulations of the present invention in any effective concentration, including, for example, in a concentration range of about 5% to about 50% (w/v).

Optionally, a chelating agent and/or a soluble antioxidant may be included in the SEDDS for use in the invention. Chelating agents may be added to enhance the stability of a hydrophobic drug in the SEDDS composition. Suitable optional chelating agents include any pharmaceutically acceptable chelating agent, such as citric acid, maleic acid, succinic acid, tartaric acid, EGTA (ethylene glycol-bis ((3-aminoethyl ether)tetraacetic acid, or egtazic acid) and EDTA (ethylene diamine tetraacetic acid, or edetic acid). Such chelating agents are available in various forms, e.g., as sodium or potassium salts or as the free acids. Such chelating agents may be used in the formulations of the present invention in any effective concentration, including, for example, in a concentration range of between 0.01% and 10% (w/v).

For preparing an SEDDS formulation, for example, an absorption promoter such as sodium salicylate, sodium deoxycholate, sodium myristate, or sodium dodecyl sulfate.

The SEDDS formulations may contain an auxiliary solvent such as ethanol, propylene glycol, polyethylene glycol, diethylenetriaminepentaacetic acid, diethanolamine, triethanolamine, ethylenediamine, monoethanolamine, or N,N-dimethylacetamide.

The SEDDS formulation may be prepared by dissolving the drug in a mix of oil, surfactant and cosolvent.

The biologically active material used in the compositions of the present invention may comprise any known biologically active material. The term "biologically active ingredient" is meant to cover any pharmaceutical or other active ingredient for administration to humans or animals, in particular to warm-blooded animals. The biologically active material may be an active pharmaceutical ingredient (API), which comprises include natural, semi-synthetic or synthetic molecules. In some embodiments, the biologically active material comprises two or more active pharmaceutical ingredients (APIs) in combination with one another. Other biologically active ingredients include ingredients that have an effect on the general well-being or have an effect on the outer appearance (cosmetic) such as the skin, hair, lips, and eyes. Such ingredients include any agents for use in cleansing, beautifying, promoting attractiveness, or altering the appearance, for example moisturizers, oils, anti-wrinkle agents, fragrances, and the like. Also included are ingredients for nutritious applications (in particular the so-called "nutraceutical" ingredients). Such ingredients include food supplements such as, for example, dietary food supplements, vitamins, minerals, fiber, fatty acids, and amino acids. Examples of such ingredients are Vitamin C, omega-3 fatty acids, carotenes, and flavonoids. The term "biologically active" in relation to compositions for cosmetic or nutricious applications also includes activity relating to the improvement of the outer part of the body, in particular of the dermis, as well as the general well-being of an individual.

In one embodiment, the active ingredient has a molecular weight below about 1,000 (daltons), or below about 800, for example a molecular weight in the range of about 150 to about 1,000, or in the range of about 200 to about 800.

The active ingredient for use in the invention may be soluble or insoluble in water or aqueous media, in particular physiological aqueous media. According to generally accepted standards, any solvent solubility is defined as the amount of a solvent (g) required to dissolve 1 g of a compound, whereby the following solubility qualifications are defined: 10-30 g ("soluble"); 30-100 g ("sparingly soluble"); 100-1000 g ("slightly soluble"); 1000-10000 g ("very slightly soluble" or "poorly soluble") and more than 10000 g (practically insoluble).

In one embodiment, the active ingredient is soluble or insoluble in water or aqueous media, in particular physiological aqueous media. In one embodiment, the pharmaceutically active ingredient belongs to the so-called BCS classes I through IV. Classes I and III are the soluble drugs. The Biopharmaceutical Classification System (BCS) classifies drug substances based on their aqueous solubility and intestinal permeability into four classes: Class I—High Permeability, High Solubility; Class II—High Permeability, Low Solubility; Class III—Low Permeability, High Solubility; Class IV—Low Permeability, Low Solubility.

In one embodiment, the active ingredient has a partition coefficient (expressed as log P) that is in the range from 4 to 9, in the range from 3 and 8. In a further embodiment, the active ingredient has a $pK_A$ that allows the molecule to be in neutral (non-ionic form) at about pH 5-8.

Exemplary APIs include, atorvastatin, amiodarone, candesartan-cilexetil, carvedilol, clopidogrel bisulfate, dipyridamole, eprosartan mesylate, epierenone, ezetimibe, felodipine, furosemide, isradipine, lovastatin, metolazone, nicardipine, nisoldipine, olmesartan medoxomil, propafenone HCl, qinapril, ramipril, simvastatin, telmisartan, trandolapril, valsartan and other cardio-vascular active drugs; acyclovir, adefovir, dipivoxil, amphotericin, Amprenavir, cefixime, ceftazidime, clarithromycin, clotrimazole, efavirenz, ganciclovir, itraconazole, norfloxacin, nystatin, ritonavir, saquinavir and other anti-infective drugs including anti-bacterial, anti-viral, anti-fungal and anti-parasitic drugs; cisplatin, carboplatin, docetaxel, etoposide, exemestane, idarubicin, irinotecan, melphalan, mer-captopurine, mitotane, paclitaxel, valrubicin, vincristine and other drugs used in oncology; azathioprine, tacrolimus, cyclosporin, pimecrolimus, sirolimus and other immonosupressive drugs; clozapine, entacapone, fluphenazine, imipramine, nefazodone, olanzapine, paroxetine, pimozide, sertraline, triazolam, zaleplon, ziprasidone, risperidone, carbamazepine and other drugs for CNS indications; danazol, dutasteride, medroxyprogesterone, estradiol, raloxifene, sildenafil, tadalafil, testosterone, vardenafil and other drugs used for reproductive health; celecoxib, dihydroergotamine mesylate, eletriptan, ergoloidmesylates, ergotamine tartrate, nabumetone, Ibuprofen, ketoprofen, triamcinolone, triamcinolone acetonide and other anti-inflammatory and analgesic drugs; bosentan, budesonide, desloratadine, fexofenadin, Fluticasone, ioratadine, mometasone, salmeterol, xinafoate, triamcinolon acetonide, zafirlukast and other drugs for respiratory indications; and dronabinol, famotidine, glyburide, hyoscyamine, isotretinoin, megestrol, mesalamine, modafinil, mosapride, nimodipine, perphenazine, propofol, sucralfate, thalidomide, trizanidine hydrochloride and other drugs for various indications including in particular gastro-intestinal disorders, diabetes and dermatology indications. In further embodiments the APIs include ezetimimbe, glucoroniude, tadalafil, fenofibrate, danazol, itraconazole, carbamazepine, griseofulvin, nifedipin.

The active ingredients further include sugars, polysaccharides, vitamins, amino acids, peptides, prostaglandins, nucleic acids, nucleotides, nucleosides, as well as derivatives thereof. Also included are peptides, proteins, protein fragments, antibodies, small antibody fragments, and the like. The latter include Fv" fragments, single-chain Fv (scFv) antibodies, antibody Fab fragments, antibody Fab' fragments, antibody fragments of heavy or light chain CDRs, or nanobodies. Also encompassed are small oligonucleic acid or peptide molecules such as aptamers, for example DNA aptamers, RNA aptamers or peptide aptamers.

In one embodiment, the biologically active ingredient in a liquid material when loaded in the inorganic oxide material shows an increased release compared to the active ingredient as such, or to formulations containing the active ingredient and ingredients that do not influence release. Increased release may for example be an increase of 10%, or of 20%, or of 30%, or of 50%, of the weight percentage of active ingredient released under physiological conditions (pH, temperature).

In a further embodiment, the biologically active ingredient in a liquid material when loaded in the inorganic oxide material shows immediate release from the compositions of the invention, the term "immediate release" meaning, for example, a release of at least 60% of the drug under physiological conditions (pH, temperature), such as within 60 minutes or less, such as within 30 or less, or within 20 minutes or less, or within 15 minutes or less.

In the methods of making a composition of the present invention, the step of incorporating the biologically active material into the inorganic oxide material typically comprises a variety of loading methods, including the solvent method and the incipient wetness method, which methods have been described in the prior art, or mere mixing without use of any solvent or other mixing aid.

In the (slurry) solvent method the inorganic oxide material is loaded with an active ingredient by treatment with a solution of the active ingredient in a liquid material, after which the solvent is removed. The active ingredient in a liquid material thereby becomes adsorbed to the surface of the inorganic oxide material, including the surface within the pores of the inorganic oxide material. Appropriate organic solvents for use in this method include dichloromethane, 1,4-dioxane, tetrahydrofuran, 2-propanol, diethyl ether, ethyl acetate, acetonitrile, dimethylformamide, N-methylpyrrolidinone, hexane. For example, a solution containing about 50 mg of active ingredient per ml can be used for loading active ingredients in inorganic oxide material.

In the incipient wetness method, also referred to as capillary impregnation or dry impregnation the inorganic oxide material is wetted with the active ingredient in a liquid material or in a concentrated solution and is drawn into the pores by capillary action. The porous inorganic oxide materials of the invention are particularly suited for this methodology as they show strong capillary action. In many instances, no or very little solvent needs to be used thereby avoiding the removal of the solvent after the loading step. This offers an additional advantage over known liquisolid formulations, which require additional ingredients needed to help adsorption, in particular solvents, involving methods of premixing the carrier or the drug in a liquid material (lipid or SEDDS) with a solvent to improve the adsorption. The presence of solvents in medicines and other products for human or animal use are critically scrutinized while many solvents are banned. Solvents also have environmental implications as they are considered an important source of pollution.

In another embodiment, the liquid material may be loaded onto the inorganic oxide material by spraying, or any other known method of liquid adsorption onto porous materials.

The biologically active ingredient in a liquid material either with or without solvent may have a viscosity that is selected such that it can be adequately adsorbed by the inorganic oxide material, in particular in terms of speed of adsorption, sufficient loading, and the like. It may for example have a viscosity below about 250 mPa·s, or below about 100 mPa·s, or below about 10 mPa·s, or below about 5 mPa·s, or below about 1 mPa·s. The lower limit of the viscosity may be about 0.1 mPa·s, or about 0.5 mPa·s.

The inorganic oxide materials of the invention are very efficient adsorbants of biologically active ingredient in liquid form. Contrary to known porous materials, where adsorption takes place in a very short time after being brought in contact with the liquid material, the inorganic oxide materials of the invention adsorp biologically active ingredient in liquid form during longer periods of time, in particular during several hours, for example up to about 2, 3, or 4 hours. It is believed that the decrease in volume after resting is related to capillary forces that continue to draw free liquid between the particles up into the pores of the particles. This attributes to the high loading capacity of the inorganic oxide materials of the invention.

The content of the active ingredient in the inorganic oxide material materials may be in the range of about 1% to about 50%, or about 10% to about 30%, or about 15% to about 25%, for example about 20%, relative to the total weight of the loaded silica material (all percentages herein being weight/weight).

The compositions of the present invention may in one or more additional steps formulated into a final dosage form, which may vary depending upon the manner in which it is administered to the patient. Preferred are solid or semisolid dosage forms for oral administration, in particular pills, tablets, and capsulees. Such dosage forms may be suitable for providing immediate or fast in vivo release of said biologically active species, or may be suitable for controlled release. This may include one or more pharmaceutically acceptable excipients Regardless of the production method used to prepare the compositions containing a biologically active material and an inorganic oxide material in accordance with this invention, whether it is solvent-based or solventless, when the final dosage form comprises one or more pharmaceutically acceptable excipients, they may be introduced at any time during the process, including the step designed to load the biologically active material into the pores of the inorganic oxide material, or afterwards in a separate step.

The pharmaceutical compositions may also contain optional excipients. These may comprise any of the ingredients customarily employed in the art such as diluents, binding agents, granulating agents, glidants (flow aids), lubricants; disintegrants, sweeteners, flavors, and pigments to make the tablets visually attractive. Examples of such excipients include hydroxypropylmethyl cellulose, crospovidone, magnesium stearate, lactose, and talc.

The pharmaceutical compositions of the present invention may further comprise one or more pharmaceutically acceptable fillers selected, for example, from hydrocolloids (such as xanthan gum), binding agents, glidants, lubricants, surfactants and diluents.

These include for instance binding agents such as starch, gelatin, glucose, alginic acid, sodium and calcium alginates, water-soluble acrylic (co) polymers, polyvinyl-pyrrolidone, polyaminoacids, ethylene-vinyl acetate copolymers and the like; natural and synthetic mineral fillers or glidants such as silica, magnesium silicates such as talc, diatomaceous earth, aluminum silicate such as kaolinite, montmorillonite or mica, magnesium aluminum silicate such as attapulgite and vermiculite, carbon such as charcoal, sulphur and highly dispersed silicic acid polymers; water-soluble diluents such as lactose, sorbitol and the like.

The compositions of the present invention may also be formulated into forms suitable for topical application such as an ointment, a cream, a gel, a liniment or balm, etc. . . .

The present invention is further directed to methods of using any of the herein disclosed compositions. In some embodiments, the compositions, in particular the pharmaceutical compositions, of the present invention may be used as medicaments, in particular may be used as medicaments via the oral route.

The present invention a method of administering a composition to a patient so as to deliver at least one biologically active material to the patient, wherein the composition comprises at least one pharmaceutical dosage formulating ingredient of a porous inorganic oxide material containing a biologically active ingredient in liquid form, wherein the inorganic oxide material has the oil adsorption, the intraparticle pore volume, and BET surface area, as specified herein. The compositions in this method are preferably administered by various means, including by oral, buccal, sublingual, periodontal, vaginal, intrauterine, rectal, pulmonary, nasal, inhalation, intraocular, ophthalmic, auricular, and topical means.

One of the reasons for improved release of the biologically active material from the compositions of the present invention is due to the improved desorption of the liquid material from the inorganic oxide material. The presence of pores within the inorganic oxide materials (i.e., intraparticle porosity) that have certain features allows for a substantial amount of the biologically active ingredient to be adsorbed and then released. For example, the pore size distribution of the present inorganic oxide material is narrow (i.e., a small relative span), which allows for a number of pores to readily adsorb and desorb the liquid material. This contrary to known porous materials where the biologically active ingredient is adsorbed into or released from interstitial voids between lumps or particles of the carrier material, the size and shape of which are more aleatory and offer less room for loading molecules. This causes not only less loading capacity, but also less regular release profiles. Other factors that influence release are viscosity of the active ingredient in liquid form and the isoelectric point (log P).

The compositions in accordance with the invention provide attractive drug delivery properties. They provide desirable desorption and/or dissolution rate profiles for a variety of biologically active materials (e.g., APIs). In some embodiments, the biologically active material exhibits a percent release desorption and/or dissolution rate of about 20 or greater within about 15 minutes of an initial time of contact with a dissolution medium. In some embodiments, the biologically active material exhibits a percent release dissolution rate of about 25 or greater (or about 30 or greater; or about 35 or greater) within about 15 minutes of an initial time of contact with a dissolution medium.

Further, in some embodiments, the biologically active material exhibits a percent release dissolution rate of about 20 or greater about 30 minutes after an initial time of contact with a dissolution medium. In some embodiments, the biologically active material exhibits a percent release dissolution rate of about 30 or greater about 30 minutes after an initial time of contact with a dissolution medium.

In some embodiments, the biologically active material exhibits a percent release dissolution rate of about 10 or greater about 60 minutes after an initial time of contact with a dissolution medium. In some embodiments, the biologically active material exhibits a percent release dissolution rate of about 15 or greater (or about 20 or greater) about 60 minutes after an initial time of contact with a dissolution medium.

The compositions of the present invention in many instances show immediate release of the active ingredient but may be turned into controlled release compositions for example by coating the compositions with a suitable polymer. When mixing compositions with selected polymer coatings mixed release patterns can be obtained such as a combination of immediate and sustained release.

The inorganic oxide material may comprise two or more different and distinct types of porous particles with each distinct type of porous particles providing a specific desorption and/or dissolution rate profile for a single biologically active material (or two or more different biologically active materials) so as to form a composite desorption and/or dissolution rate profile.

A further aspect of this invention concerns particles of a inorganic oxide material, wherein the inorganic oxide material wherein the inorganic oxide material has the oil adsorption, the intraparticle pore volume, and BET surface area, as specified herein.

The compositions of the present invention not only show high loadability of drugs in liquid form, they moreover show higher bulk density compared to existing liquisolid systems. Further favorable properties include the excellent adsorptive capacity of the inorganic oxide material of the invention and the increased stability of the active ingredient. These advantages are in particular offered by the compositions of the invention in the form of particles.

The compositions of the present invention can also be used in dermatology and cosmetic applications because of their good skin-compatability and lack of unpleasant skin feel.

The following examples are meant to illustrate the present invention and should not be construed as a limitation of its scope.

Example 1

Sodium water glass with a Na content of 24.5% w/v and sulfuric acid of 45% w/v were mixed with a molar ratio of 0.85 to 0.99. After completion of the poly condensation the raw silica gel was crushed into pieces of several cm sizes. Then the by-product sodium sulfate was removed by washing the silica gel/sodium sulfate mixture with clear water. The aging of the silica by Oswald ripening took place in a water bath for 3-11 hours at 70-80° C. and at pH between 8 and 9. After the liquid/solid separation the formed silica hydro gel was crushed down to a particle size of about 300 μm. The subsequent drying step controlled the formation of the pore volume. In order to achieve pore volumes of about 1.7 cm³/g rapid drying for less than 4 seconds at a process air temperature of 180 was needed and was conducted in a lab flash dryer type LABSPINFLASH (APV/Denmark). Silicas with pore volumes of <1 cm³/g were made by slow drying (packed bed drying) in a lab drying chamber at 100° C. for 4 h.

The following silica particles shown in Table 1 below were used in the subsequent examples.

TABLE 1

| Identification | S1 | S2 |
|---|---|---|
| Malvern | | |
| D10 (μm) | 75 | 23-41 |
| D50 (μm) | 102-120 | 48-65 |
| D90 (μm) | 174 | 76-96 |
| Pore Size (nm) Desorption (BJH) | 25 | 25 |
| PV (ml/g) | 1.6-1.95 | 1.6-1.95 |
| Relative Span | 0.71 | 0.71 |
| BET SA (m²/g) | 280-355 | 280-355 |
| APD (Calc) (Å) | 250 | 250 |

The D10, D50 and D90 values indicate the $10^{th}$, $50^{th}$ and $90^{th}$ percentiles of the weight of the particle diameter distribution. These values were obtained from a Malvern™ Mastersizer 2000 instrument available from Malvern Instruments Ltd. PV: pore volume; SA: surface area; APD: average pore diameter; BET SA: surface area; and Relative Span are determined using BJH nitrogen adsorption at a pressure of 0.995 using an ASAP 2420HV accelerated surface area and porosimetry system available from Micromeretics Instrument Corporation.

Example 2

Procedure: 2 to 5 g (based on bulk density) of the solid carrier material was placed in a 100 ml beaker and the oil or surfactant was added drop wise from a Burette, while mixing with spatula according to ASTM D281. The addition of oil or surfactant was continued until a thick paste-like mass formation. The addition of oil or surfactant was stopped when the mass appeared to contain excess oil. The Burette reading was recorded when the mass contained no excess oil or surfactant. The adsorption capacity was calculated using the below equation:

$$\text{Oil adsorption (g/100 g)} = \frac{\text{Volume of oil added (ml)} \cdot SG \text{ of oil } 100}{\text{Weight of sample (g)}}$$

The following table lists oils and and their adsorption capacity on Sample S1 material as well as the specific gravity of the oils.

TABLE 2

| No. | Name of the Oil | Specific gravity (g/mL) | Adsorption capacity (g/100 g) |
|---|---|---|---|
| 1 | Raw linseed oil | 0.930 | 294 |
| 2 | Eucalyptus oil | 0.915 | 328 |
| 3 | Lemon grass oil | 0.895 | 287 |
| 4 | Peppermint oil | 0.890 | 307 |
| 5 | Castor oil | 0.960 | 316 |
| 6 | Sesame oil | 0.923 | 298 |
| 7 | Olive oil | 0.920 | 305 |
| 8 | Clove oil | 1.045 | 390 |
| 9 | Oleic acid | 0.895 | 300 |
| 10 | dl-α-Tocopherol | 0.950 | 292 |
| 11 | Captex 355 | 0.940 | 315 |
| 12 | Labrafac PG | 0.919 | 304 |
| 13 | Miglyol 812 | 0.940 | 319 |
| 14 | Capmul MCM | 0.995 | 303 |

The following table lists surfactants and their adsorption capacity on Sample S1 material as well as the specific gravity of the surfactants.

TABLE 3

| No. | Name of the Surfactant | Specific gravity (g/mL) | Oil adsorption S1 (g/100 g) |
|---|---|---|---|
| 1 | Transcutol HP | 0.987 | 295 |
| 2 | Solutol HS 15 | 1.04 | 310 |
| 3 | Cremophor EL | 1.05 | 317 |
| 4 | Labrasol | 1.064 | 326 |
| 5 | Labrafil M-1944CS | 0.943 | 292 |
| 6 | Capryol 90 | 0.942 | 300 |

In comparison, other carriers were tested for oil adsorption and following results were obtained.

TABLE 4

| g. oil/100 g carrier | Oleic acid | Linseed oil | Tocopherol | Cremophor EL | Labrasol |
|---|---|---|---|---|---|
| Fujicalin | 113 | 127 | 103 | 140 | 138 |
| MCC PH 101 | 120 | 102 | 98 | 123 | 131 |
| Galen IQ 721 (sugar based carrier) | 63 | 69 | 57 | 67 | 69 |
| Talc | 62 | 57 | 54 | 70 | 67 |

Example 3

Following the procedure of Example 2, the Cremophor and Labrafil loaded materials were allowed to rest for 3 hours and then tested for free flowing properties. The results are shown in Tables 5 and 6.

TABLE 5

| Flow parameters (Cremophor Loaded 1.5:1) | S1 (250 Å, 110 μm) | S2 (250 Å, 50 μm) |
|---|---|---|
| Oil added (mL) | 7.14 | 7.14 |
| Carrier material (g) | 5 | 5 |
| B. Density | 0.632 | 0.631 |
| T. Density | 0.702 | 0.742 |
| C.I | 10 | 15 |
| (USP rating) | (Excellent) | (Good) |
| H.R | 1.11 | 1.17 |
| (USP rating) | (Excellent) | (Good) |

TABLE 6

| Flow parameters (Labrafil loaded 1.5:1) | S1 | S2 |
|---|---|---|
| Oil added (mL) | 7.95 | 7.95 |
| Carrier Material (g) | 5 | 5 |
| B. Density | 0.615 | 0.616 |
| T. Density | 0.724 | 0.724 |
| C.I (USP rating) | 15 (Good) | 15 (Good) |
| H.R (USP rating) | 1.17 (Good) | 1.17 (Good) |

Bulk Density is measured by USP 616 Method 1 using a 250 ml graduated cylinder (USP30-NF25). Tapped density is measured by USP 616 Method 2 (250 taps per minute) using a 250 ml graduated cylinder, with an ETD-1020 Tap Density Tester available from Electrolab. USP rating is an observed measure of powder flow and is rated according to the following Table 7.

TABLE 7

| Compressibility Index (%) | Flow Character | Hausner Ratio |
|---|---|---|
| <10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Very, very poor | >1.60 |

Example 4

Following the procedure of Example 2, 10 grams of Sample S1 is loaded with 16.25 ml of sesame oil, which yield a 1:1.5 ratio of inorganic oxide material to oil. The volume of the mixture decreases from 65 ml to 50 ml over a period of 10 hours, which is a decrease in over 23% as shown in FIG. 1.

Example 5

Figure 2:
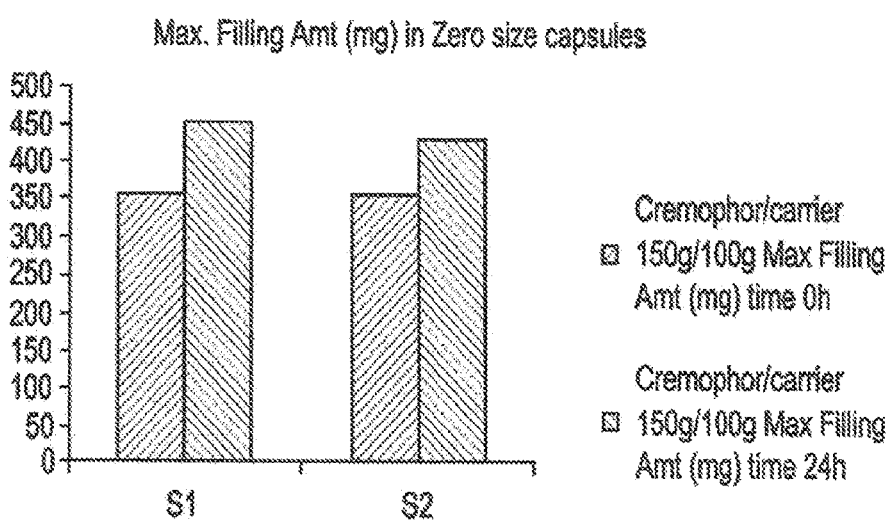
FIG. 2 graphically displays capsule loading capacity change before and after resting of an exemplary composition of the present invention according to Example 4.

The Cremophor and Labrafil loaded materials of Example 3 were loaded into zero size capsules manually using a capsule filling tray, such as the Cap-M-Quick available from Empty Caps Company. As can be seen from FIG. 2, there is a significant difference between the filling amounts before and after resting of the material. The amounts of material loaded into the capsules are set forth in Tables 8 and 9.

TABLE 8

| Flow parameters (Cremophor Loaded 1.5:1) | S1 (250 Å, 110 μm) | S2 (250 Å, 50 μm) |
|---|---|---|
| Oil added (mL) | 7.14 | 7.14 |
| Carrier Material (g) | 5 | 5 |
| Filling Amount (mg) After resting | 451 | 429 |
| Filling Amount (mg) Before resting | 357 | 357 |

TABLE 9

| Flow parameters (Labrafil loaded 1.5:1) | S1 | S2 |
|---|---|---|
| Oil added (mL) | 7.95 | 7.95 |
| Carrier Material (g) | 5 | 5 |
| Filling Amount (mg) After resting | 421 | 421 |
| Filling Amount (mg) Before resting | 366 | 366 |

Example 6

Figure 3:
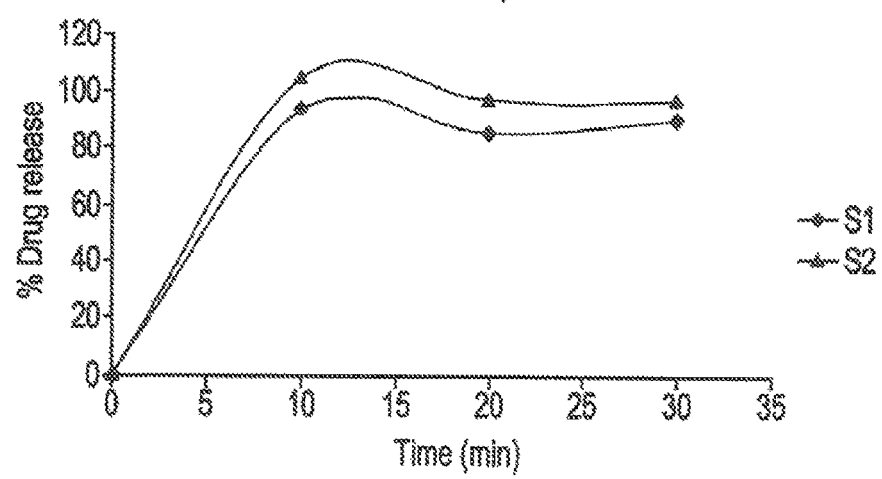
FIG. 3 graphically displays a release profile of acetaminophen from an exemplary composition of the present invention according to Example 6.

Following the procedure of Example 2, acetaminophen and ascorbic acid loaded material was obtained and labeled carriers S1 and S2, respectively The drug release from carriers S1 and S2 was determined as follows:

The acetaminophen loaded carrier (S1) was subjected to dissolution studies as per USP 30 for Acetaminophen Tablets for 30 min. Dissolution test conditions comprised of use of USP dissolution apparatus 2 (Paddle) operated at speed of 50 RPM for 30 minutes. Dissolution medium was 900 ml of pH 5.8 Phosphate Buffer at 37±0.5° C. For each carrier, 100 mg of the weighed amount of drug loaded carrier was used to dissolution studies. Aliquots (5 ml) were withdrawn at 10, 20, 30 minute time intervals, filtered and diluted with dissolution fluid. Absorbance of aliquots was determined spectrometrically at λmax 243 nm. The release profile is illustrated in FIG. 3 The drug release from the both carriers S1 and S2 met the USP criteria (NLT 80% in 30 minutes).

Figure 4:
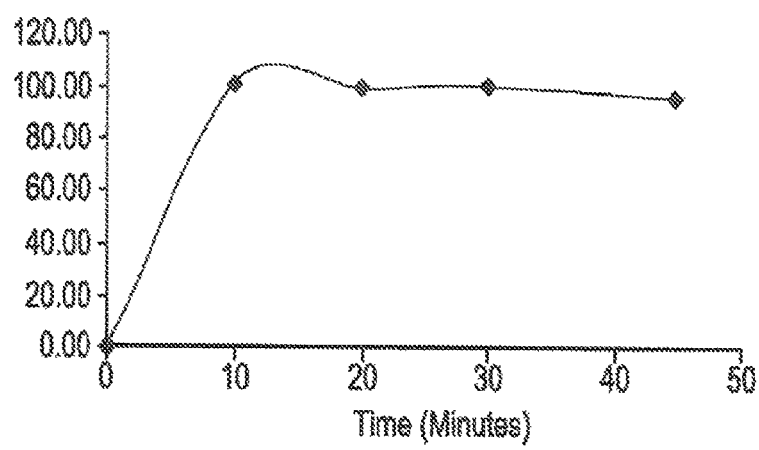
FIG. 4 graphically displays a release profile of ascorbic acid from an exemplary composition of the present invention according to Example 6, FIG. 5 graphically displays the release profile Glyburide from a solid SEDDS system of the present invention according to Example 8.

The ascorbic acid loaded carrier (S1) was subjected to dissolution studies as per USP 30 for Ascorbic acid Tablets for 45 min. Dissolution test conditions comprised of use of USP dissolution apparatus 2 (Paddle) operated at speed of 50 RPM for 45 minutes. Dissolution medium was 900 ml of water at 37±0.5° C. For each carrier, 100 mg of the weighed amount of drug loaded carrier was used to dissolution studies. Aliquots (5 ml) were withdrawn at 10, 20, 30 minute time intervals, filtered and diluted with water. Absorbance of aliquots was determined spectrometrically at λmax 266 nm. The release profile is illustrated in FIG. 4. The drug release from the both carriers S1 and S2 met the USP criteria (NLT 75% in 45 minutes).

Example 7

Oil release or desorption: The carrier material used in the following trials was the material designated S1 prepared in Example 1. 2 grams of oil loaded carrier (1:1, w/w) prepared pursuant to method of Example 2 was mixed with 6 ml water in a beaker, vortexed during 1 hour, and centrifuged at 5000 RPM for 10 min in a Heraeus Multifuge 1S-R centrifuge available from Thermo Electron Corporation. The supernatant, i.e. oil+water, was transferred into a petry dish and dried in hot air oven up to constant weight.

The results, which are based upon the w/w % release obtained in the trials, are as follows. For sesame oil, 81% of the oil is released from the carrier material or inorganic oxide, and for Miglyol 812, 81.3% of the oil is released from the carrier material or inorganic oxide.

Example 8

Solid SEDDS System Loading and Release (or Desorption): The carrier materials used in the following trials was the materials designated as S1 and S2 in Example 1. A liquid SEDDS system was made up containing 0.6 g of Glyburide as the API component, 15 g of Capryol®90 as the oil/vehicle component, 54.4 g of Trascutol® HP as a co-surfactant, and 30 g of Tween® 20 as a surfactant. This liquid SEDDS system was loaded onto S1 and S2 by accurately weighing the required quantities of carrier and liquid SEDDS in the ratio of 1:1. Carrier and Liquid SEDDS were pre-heated at 60° C. for 15 min, prior to mixing. Liquid SEDDS was added slowly to the carrier under stirring with metallic spatula. The prepared mixture was kept aside for around 24 hr to get free flowing powder.

Figure 5:
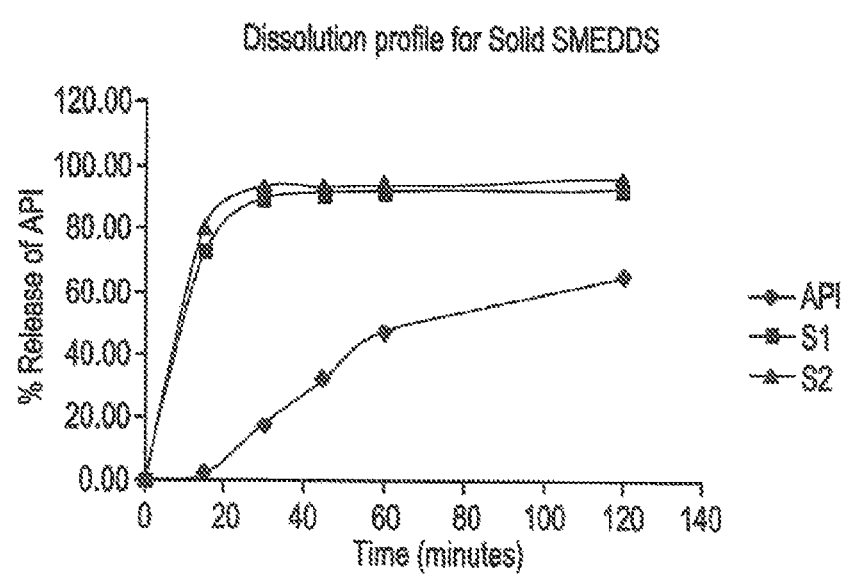

The liquid SEDDS loaded carriers (S1) and (S2), as well as non-micronized Glyburide were subjected to dissolution studies as per USP<711> for 120 minutes. Dissolution test conditions comprised of use of USP dissolution apparatus 2 (paddle) operated at a speed of 75 RPM. Dissolution medium was 500 ml of pH 9.5 Borate Buffer (0.05M) at 37±1° C. For each carrier, a weighed amount of loaded carrier or API (non-micronized Gyburide) with an weight equivalent basis of 5 mg Gyburide were used for the dissolution studies. 5 ml Aliquots were withdrawn at 20, 30, 45, 60, and 120 minutes, filtered through 0.45µ syringe filter and diluted with dissolution fluid. Samples were analyzed using HPLC (Waters Acquity H-class) using Grace Vision HT high load C18 column, Rocket Format, (53×7 mm, 3 µm) as stationary phase and Acetonitrile: o-phosphoric acid 0.4% in water (50:50) as mobile phase at flow rate of 1.5 mL/min with injection volume of 50 µl. Samples were detected at λmax 226 nm. The release profile is illustrated in FIG. 5. The drug release from both carriers S1 and S2 met the USP criteria (NLT 70% drug release within 45 minutes, and NMT 3% relative SD).

oil loaded carrier component in tablet formulations. To deliver oil in tablet dosage form, tablets were made with two different processes: direct compression (DC) and wet granulation (WG).

Direct compression tablets were obtained by accurately weighed the quantities of excipients for blend preparation. Diluent (MCC) and Oil loaded carriers were sieved through #40 mesh and mixed well for approximately 5 min. Binders and disintegrant were sieved through #40 mesh and added to the blend, then mixed well for approximately 5 min. Glidant was passed through #40 mesh and added to the blend and mixed well for 5 min. Lubricant was sieved through #60 mesh and added to the blend and mixed well for approximately 2 min. This final blend was used for the compression of the tablets.

Wet granulation tablets were obtained by accurately weighed the quantities of excipients for blend preparation. Diluents (MCC) and Oil loaded carriers were sieved through #40 mesh and mixed well for approximately 5 min. Disintegrant was sieved through #40 mesh and added to the blend, then mixed well for approximately 5 min. Binder (starch/pregelatinized starch) was prepared in a water solution (5%). Granules were then prepared by mixing Prepared diluents/oil loaded carrier/disintegrant blend with the binder solution. Granules were dried at 50° C. to achieve LOD of 5-7%. Dried granules were passed through #20 mesh. Glidant was passed through #40 mesh and added to the blend and mixed well for 5 min. Lubricant (what material) was sieved through #60 mesh and added to dried granules and mixed well for approximately 2 min. This final blend was used for the compression of the tablets.

Tablets were prepared using a Parle Elizabeth tools Pvt Ltd, Eliza press 200 multi tooling single rotary tablet press operated at a Speed of 5 rpm, compression force of 20 kN, ejection force <70N, and with a 12 mm round bioconcave, D-tooling punch. The formulations tabletted are listed in Table 10 below.

TABLE 10

| Formulation Identifier | DCA | DCB | DCC | DCD | DCE | WGA | WGB |
|---|---|---|---|---|---|---|---|
| Tabletting method (DC = Direct Compression; WG = Wet Granulation) | DC | DC | DC | DC | DC | WG | WG |
| Oil loaded Carrier S2 (wt %) | 20 | 20 | 30 | 30 | 40 | 40 | 50 |
| MCC PH102 (wt %) | 70.5 | 70.5 | 60.5 | 60.5 | 45.5 | 50.5 | 40.5 |
| PVPK30 (wt %) | 5 | 5 | 5 | 5 | 0 | 0 | 0 |
| Pregelatinized starch (wt %) | 0 | 0 | 0 | 0 | 10 | 5 | 5 |
| AcDiSol (wt %) | 3 | 3 | 3 | 3 | 3 | 3 | 3 |
| Syloid 244FP (wt %) | 1 | 1 | 1 | 1 | 1 | 1 | 1 |
| Mg St (wt %) | 0.5 | 0.5 | 0.5 | 0.5 | 0.5 | 0.5 | 0.5 |
| Compression force (kN) | 15 | 20 | 15 | 20 | 20 | 20 | 20 |
| Weight (mg) | 500 | 500 | 500 | 500 | 500 | 500 | 500 |

To define the maximum amount of preloaded carrier in a tablet while maintaining optimum tabletting properties, the following experiments as shown in example 9 and 10 were performed:

Example 9

The carrier materials used in the following trials was the material designated S2 in Example 1. Cremophor® EL was the liquid lipid that was loaded on to the silica. Silica S2 was loaded pursuant to method of Example 8 and was used as the Tablet hardness for all formulations was measured with EH 01 tablet hardness tester (Electrolab, India). The hardness for tested formulations are listed in Table Y below.

TABLE 11

| Formulation Identifier | DCA | DCB | DCC | DCD | DCE | WGA | WGB |
|---|---|---|---|---|---|---|---|
| Hardness (N) | 83-93 | 83-97 | 68-76 | 84-91 | 60-70 | 80 | 30 |

In all cases the tablets met the USP specifications for Weight variation (NMT 5%), Firability (<%), and disintegration time (<15 min).

Example 10

High Concentration of Liquid Lipids Loaded onto Carrier and Compressed into Tablets: The carrier materials used in the following trials was the material designated 52 in Example 1. Tocopherol was the liquid lipid that was loaded on to the silica. Silica S2 was loaded with liquid lipid pursuant to method of Example 8 and was used as the oil loaded carrier component in tablet formulations. PVP30 was dispersed in ethanol (100 mL) and added upon oil loaded carrier. Prepared blend was mixed thoroughly and allowed to dry at 50° C. Additional excipients were added pursuant to the method in Example 9 to obtain a direct compression blend with the following composition: 70% Tocopherol loaded silica S2 (1:1 loaded), 12.5% MCCPH102, 14% PVP30, 2% AcDiSol, 1% SYLOID® 244FP, 0.5% Magnesium Stearate. Tablets were prepared using a Parle Elizabeth tools Pvt Ltd, Eliza press 200 multi tooling single rotary tablet press operated at a Speed of 5 rpm, compression force of 20 kN, ejection force <70N, and with a 12 mm round bioconcave, D-tooling punch.

Tablet hardness for all formulations was measured with EH 01 tablet hardness tester (Electrolab, India) at tablet weight of 500±5 mg. Tablet hardness results for these tablets was 40N. Friability was 0% and disintegration time was <1 min.

Example 11

Oil Release (Tocopherol) from Tablets: The carrier materials used in the following trials was the material designated S2 in Example 1. Tocopherol was the liquid lipid that was loaded on to the silica. Silica S2 was loaded with liquid lipid pursuant to method of Example 8 and was used as the oil loaded carrier component in tablet. Tablets were prepared pursuant to the method in example 10. Tochopherol concentration in the tablet was 100 mg.

Tablets prepared were subjected to dissolution studies pursuant to the method described in Example 8. An aliquot of 2 mL was withdrawn at predetermined time interval and filtered through 0.22μ membrane filter. The dissolution samples were analyzed by using HPLC (Waters UPLC Wavelength: 294 nm Column: Rocket Format, 53×7 mm, 3μ) Mobile Phase: 85% ACN: 10% MeOH: 5% H2O.)

The Tocopherol release at 45 min was ≈100%.

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 30%, 40%, 5% . . . 50%, 51%, 52% . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

The invention claimed is:

1. A composition comprising porous amorphous silica particles containing (i) a biologically active ingredient in liquid form or (ii) a biologically active ingredient within a liquid material, wherein the amorphous silica particles possess:
   (a) an oil adsorption of about 100 to less than 400 ml/100 g as measured using test method ASTM D281;
   (b) pores having a pore volume, as measured by nitrogen porosimetry, of about 0.5 cm$^3$/g or greater; and
   (c) a pore size distribution having a relative span of from 0.1 to about 1.5;
   wherein said composition is free flowing and comprises a weight ratio (I):(II) of (I) (i) the biologically active ingredient in liquid form or (ii) the biologically active ingredient within the liquid material to (II) amorphous silica particles of at least 1.5:1.

2. A composition according to claim 1 which is a pharmaceutical composition additionally comprising at least one pharmaceutical dosage formulating ingredient.

3. A composition comprising porous amorphous silica particles containing (i) a biologically active ingredient in liquid form or (ii) a biologically active ingredient within a liquid material, wherein the amorphous silica particles possess:
   (a) an oil adsorption of about 100 to less than 400 ml/100 g as measured using test method ASTM D281;
   (b) pores having a pore volume, as measured by nitrogen porosimetry, of about 0.5 cm$^3$/g or greater;
   (c) a median pore diameter of 5 nm to 30 nm; and
   (d) a pore size distribution having a relative span of from 0.1 to about 1.5;
   wherein said composition is free flowing and comprises a ratio (I):(II) of (I) (i) the biologically active ingredient in liquid form or (ii) the biologically active ingredient within the liquid material to (II) amorphous silica particles of at least 1:1.

4. A composition comprising porous amorphous silica particles containing (i) a biologically active ingredient in liquid form or (ii) a biologically active ingredient within a liquid material, wherein the amorphous silica particles possess:
   (a) an oil adsorption of about 100 to less than 400 ml/100 g as measured using test method ASTM D281;
   (b) pores having a pore volume, as measured by nitrogen porosimetry, of about 0.5 cm$^3$/g or greater;
   (c) a median particle size of from 3 microns to 300 microns; and
   (d) a pore size distribution having a relative span of from 0.1 to about 1.5;
   wherein said composition is free flowing and comprises a ratio (I):(II) of (I) (i) the biologically active ingredient in liquid form or (ii) the biologically active ingredient within the liquid material to (II) amorphous silica particles of at least 1:1.

5. A composition comprising porous amorphous silica particles containing (i) a biologically active ingredient in liquid form or (ii) a biologically active ingredient within a liquid material, wherein the amorphous silica particles possess:
(a) an oil adsorption of about 100 to less than 400 ml/100 g as measured using test method ASTM D281;
(b) pores having a pore volume, as measured by nitrogen porosimetry, of about 0.5 cm$^3$/g or greater; and
(c) a pore size distribution having a relative span of from 0.1 to about 1.5;
wherein said composition is free flowing and comprises a weight ratio (I):(II) of (I) (i) the biologically active ingredient in liquid form or (ii) the biologically active ingredient within the liquid material to (II) amorphous silica particles of at least 1:1, and
wherein said composition, after mixing the amorphous silica particles and (i) the biologically active ingredient in liquid form or (ii) the biologically active ingredient within the liquid material, decreases in volume of at least 15% after resting up to 48 hours.

6. A composition comprising porous amorphous silica particles containing (i) a biologically active ingredient in liquid form or (ii) a biologically active ingredient within a liquid material, wherein the amorphous silica particles possess:
(a) an oil adsorption of about 100 to less than 400 ml/100 g as measured using test method ASTM D281;
(b) pores having a pore volume, as measured by nitrogen porosimetry of about 0.5 cm$^3$/g or greater; and
(c) a pore size distribution having a relative span of from 0.1 to about 1.5;
wherein said composition is free flowing and comprises a weight ratio (I):(II) of (I) (i) the biologically active ingredient in liquid form or (ii) the biologically active ingredient within the liquid material to (II) amorphous silica particles of at least 1:1, and
wherein said composition, after mixing the amorphous silica particles and (i) the biologically active ingredient in liquid form or (ii) the biologically active ingredient within the liquid material, increases in bulk density by at least 15% after resting up to 48 hours.

7. The composition according to claim 3, wherein the porous amorphous silica particles comprise a pore size distribution having a relative span of about 1.0 or less.

8. The composition according to any one of claims 1 and 2 to 7, wherein the amorphous silica particles comprise a BET surface area, as measured by nitrogen adsorption, of about 200 m$^2$/g or greater.

9. The composition according to any one of claims 1, 2 and 4 to 7, wherein the amorphous silica particles comprise pores having a mean pore diameter in the range of about 5 nm to about 30 nm.

10. The composition according to any one of claims 1 and 2 to 7, wherein the amorphous silica particles comprise a mean particle size of from about 3 μm to about 5 mm.

11. The composition according to any one of claims 1 and 2 to 7, wherein the liquid material comprises at least one of: lipid materials, non-volatile solvents, and surfactants.

12. The composition according to any one of claims 1 and 2 to 7, wherein said amorphous silica particles containing (i) the biologically active ingredient in liquid form or (ii) the biologically active ingredient within the liquid material form a powder having a Carr index of equal or lower than 25.

13. The composition according to any one of claims 1 and 2 to 7, wherein said porous amorphous silica particles are non-ordered.

14. The composition according to any one of claims 1 and 2 to 7, wherein the composition, after mixing the amorphous silica particles and (i) the biologically active ingredient in liquid form or (ii) the biologically active ingredient within the liquid material, increases in bulk density of at least 15% after resting up to 24 hours.

15. The composition according to any one of claims 1 and 2 to 7, wherein the biologically active ingredient is an active pharmaceutical ingredient comprising atorvastatin, amiodarone, candesartan-cilexetil, carvedilol, clopidogrel bisulfate, dipyridamole, eprosartan mesylate, epierenone, ezetimibe, felodipine, furosemide, isradipine, lovastatin, metolazone, nicardipine, nisoldipine, olmesartan medoxomil, propafenone HCl, qinapril, ramipril, simvastatin, telmisartan, trandolapril, valsartan, a cardio-vascular active drug, acyclovir, adefovir, dipivoxil, amphotericin, amprenavir, cefixime, ceftazidime, clarithromycin, clotrimazole, efavirenz, ganciclovir, itraconazole, norfloxacin, nystatin, ritonavir, saquinavir, an anti-bacterial drug, an anti-viral drug, an anti-fungal drug, an anti-parasitic drug, cisplatin, carboplatin, docetaxel, etoposide, exemestane, idarubicin, irinotecan, melphalan, mer-captopurine, mitotane, paclitaxel, valrubicin, vincristine, an oncology drug, azathioprine, tacrolimus, cyclosporin, pimecrolimus, sirolimus, an immunosuppressive drug, clozapine, entacapone, fluphenazine, imipramine, nefazodone, olanzapine, paroxetine, pimozide, sertraline, triazolam, zaleplon, ziprasidone, risperidone, carbamazepine, a drug for treating central nervous system (CNS) diseases, danazol, dutasteride, medroxyprogesterone, estradiol, raloxifene, sildenafil, tadalafil, testosterone, vardenafil, a drug used for reproductive health, celecoxib, dihydroergotamine mesylate, eletriptan, ergoloidmesylates, ergotamine tartrate, nabumetone, ibuprofen, ketoprofen, triamcinolone, triamcinolone acetonide, an anti-inflammatory drug, an analgesic drug, bosentan, budesonide, desloratadine, fexofenadin, fluticasone, ioratadine, mometasone, salmeterol, xinafoate, triamcinolon acetonide, zafirlukast, a drug for treating respiratory indications, dronabinol, famotidine, glyburide, hyoscyamine, isotretinoin, megestrol, mesalamine, modafinil, mosapride, nimodipine, perphenazine, propofol, sucralfate, thalidomide, trizanidine hydrochloride, a drug for treating gastro-intestinal disorders, a diabetes drug, a dermatology drug, ezetimimbe, glucoroniude, tadalafil, fenofibrate, danazol, itraconazole, carbamazepine, griseofulvin, nifedipin, or any combination thereof.

16. The composition according to any one of claims 1 and 2 to 7, wherein the biologically active ingredient is a liquid.

17. The composition according to any one of claims 1 and 2 to 7, wherein the biologically active ingredient is dissolved in a non-volatile solvent or a lipid material.

18. The composition according to any one of claims 1 and 2 to 7, wherein the biologically active ingredient is formulated in a SEDDS.

19. The composition according to claim 2, wherein the amorphous silica particles comprise a pore size distribution where at least 0.5 cm$^3$/g of pore volume are from pores ranging from 10 nm to 30 nm.

20. A composition comprising porous amorphous silica particles containing (i) a biologically active ingredient in liquid form or (ii) a biologically active ingredient within a liquid material, wherein the amorphous silica particles possess:
(a) an oil adsorption of about 100 to less than 400 ml/100 g as measured using test method ASTM D281;

(b) pores having a pore volume, as measured by nitrogen porosimetry, of about 0.5 cm$^3$/g or greater; and (c) a pore size distribution having a relative span of from 0.1 to about 1.5;

wherein, after mixing the amorphous silica particles and (i) the biologically active ingredient in liquid form or (ii) the biologically active ingredient within the liquid material and then resting for at least 2 hours, at least about 400 mg of said composition is loaded into a zero size capsule.

21. A composition comprising porous amorphous silica particles containing (i) a biologically active ingredient in liquid form or (ii) a biologically active ingredient within a liquid material, wherein the amorphous silica particles possess:

(a) an oil adsorption of about 100 to less than 400 ml/100 g as measured using test method ASTM D281;

(b) pores having a pore volume, as measured by nitrogen porosimetry, of about 0.5 cm$^3$/g or greater;

(c) a ratio (I):(II) of (I) (i) the biologically active ingredient in liquid form or (ii) the biologically active ingredient within the liquid material to (II) the amorphous silica particles of at least 1:1; and (d) a pore size distribution having a relative span of from 0.1 to about 1.5;

wherein said composition is free flowing and at least 65% of (i) the biologically active ingredient in liquid form or (ii) the biologically active ingredient within the liquid material is desorbed from the amorphous silica particles upon desorption according to the methodology and time limits described in test method USP 30.

22. A method of making the composition of claim 1, said method comprising:

incorporating (i) the biologically active ingredient in liquid form or (ii) the biologically active ingredient within the liquid material into the porous amorphous silica particles.

23. A method according to claim 22 wherein the composition is a pharmaceutical composition additionally comprising at least one pharmaceutical dosage formulating ingredient.

24. The composition according to any one of claims 1 and 3 to 7, wherein the biologically active ingredient is a nutraceutical ingredient comprising a food supplement, a dietary food supplement, a vitamin, fiber, a fatty acid, an amino acid, vitamin C, omega-3 fatty acid, a carotene, or a flavonoid.

* * * * *